(12) United States Patent
Park et al.

(10) Patent No.: US 11,278,251 B2
(45) Date of Patent: *Mar. 22, 2022

(54) MEDICAL IMAGING SYSTEM AND WORKSTATION AND X-RAY DETECTOR THEREOF

(71) Applicant: SAMSUNG ELECTRONICS CO., LTD., Suwon-si (KR)

(72) Inventors: Jong-seo Park, Yongin-si (KR); Woo-sup Han, Yongin-si (KR); Sang-uk Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 129 days.

This patent is subject to a terminal disclaimer.

(21) Appl. No.: 16/036,233

(22) Filed: Jul. 16, 2018

(65) Prior Publication Data

US 2018/0317871 A1 Nov. 8, 2018

Related U.S. Application Data

(63) Continuation of application No. 14/536,775, filed on Nov. 10, 2014, now Pat. No. 10,058,297.

(Continued)

(30) Foreign Application Priority Data

Nov. 29, 2013 (KR) .................. 10-2013-0147526
Sep. 4, 2014 (KR) .................. 10-2014-0118017
Nov. 6, 2014 (KR) .................. 10-2014-0153394

(51) Int. Cl.
*A61B 6/00* (2006.01)
*G01N 23/04* (2018.01)

(52) U.S. Cl.
CPC .............. *A61B 6/4494* (2013.01); *A61B 6/42* (2013.01); *A61B 6/4208* (2013.01);
(Continued)

(58) Field of Classification Search
CPC ....... A61B 6/42; A61B 6/4208; A61B 6/4266; A61B 6/4283; A61B 6/44; A61B 6/4405;
(Continued)

(56) References Cited

U.S. PATENT DOCUMENTS 6,217,188 B1 4/2001 Wainwright et al.
6,859,521 B2 2/2005 Spahn
(Continued)

FOREIGN PATENT DOCUMENTS

CN 102274036 A 12/2011
CN 102293657 A 12/2011
(Continued)

OTHER PUBLICATIONS

Communication dated Jul. 27, 2018, issued by The State Intellectual Property Office of P.R. China in counterpart Chinese Application No. 201480072529.2.

(Continued)

*Primary Examiner* — Allen C. Ho
(74) *Attorney, Agent, or Firm* — Staas & Halsey, LLP

(57) ABSTRACT

A workstation includes a receiver configured to receive identification information of an X-ray detector from the X-ray detector; a controller configured to set assign indicator information of the X-ray detector, based on the received identification information of the X-ray detector; an output unit configured to display the set assign indicator information of the X-ray detector; and a transmitter configured to transmit the set assign indicator information of the X-ray detector to the X-ray detector. The X-ray detector includes a transmitter configured to transmit the identification infor- (Continued)

mation of the X-ray detector to the workstation; a receiver configured to receive the assign indicator information from the workstation after the transmitter transmits the identification information of the X-ray detector to the workstation; and an output unit configured to display an assign indicator based on the received assign indicator information.

21 Claims, 24 Drawing Sheets

Related U.S. Application Data

(60) Provisional application No. 61/901,692, filed on Nov. 8, 2013.

(52) U.S. Cl.
CPC .......... *A61B 6/4266* (2013.01); *A61B 6/4283* (2013.01); *A61B 6/44* (2013.01); *A61B 6/4405* (2013.01); *A61B 6/4452* (2013.01); *A61B 6/4464* (2013.01); *A61B 6/4476* (2013.01); *A61B 6/46* (2013.01); *A61B 6/461* (2013.01); *A61B 6/465* (2013.01); *A61B 6/467* (2013.01); *A61B 6/54* (2013.01); *A61B 6/542* (2013.01); *A61B 6/545* (2013.01); *A61B 6/548* (2013.01); *A61B 6/56* (2013.01); *A61B 6/563* (2013.01); *A61B 6/566* (2013.01); *G01N 23/04* (2013.01); *A61B 6/4233* (2013.01); *A61B 6/547* (2013.01)

(58) Field of Classification Search
CPC ... A61B 6/4411; A61B 6/4452; A61B 6/4494; A61B 6/46; A61B 6/461; A61B 6/465; A61B 6/467; A61B 6/54; A61B 6/542; A61B 6/545; A61B 6/548; A61B 6/56; A61B 6/563; A61B 6/566; A61B 6/4233; A61B 6/468; A61B 6/469
USPC ............ 378/91, 98, 98.8, 115, 116, 189, 62, 378/196–198; 250/370.09
See application file for complete search history.

(56) References Cited

U.S. PATENT DOCUMENTS

| | | |
|---|---|---|
| 7,192,188 B2 | 3/2007 | Maschke |
| 7,197,112 B2 | 3/2007 | Maschke |
| 7,239,685 B2 | 7/2007 | Petrick et al. |
| 7,247,859 B2* | 7/2007 | Murphy ................ A61B 6/00 250/370.09 |
| 7,298,825 B2 | 11/2007 | Omernick et al. |
| 7,324,679 B2 | 1/2008 | Moriyama |
| 7,343,001 B2 | 3/2008 | Abu Tabanjeh |
| 7,382,859 B2 | 6/2008 | Nokita et al. |
| 7,426,261 B2 | 9/2008 | Spahn |
| 7,588,369 B2 | 9/2009 | Varjonen et al. |
| 7,764,765 B2 | 7/2010 | Ohta et al. |
| 7,772,560 B2 | 8/2010 | Ohta et al. |
| 7,847,277 B2 | 12/2010 | Kito et al. |
| 7,848,490 B2 | 12/2010 | Venturino et al. |
| 7,852,985 B2 | 12/2010 | Liu et al. |
| 7,983,392 B2* | 7/2011 | Venturino ................ A61B 6/54 378/98.8 |
| 8,172,461 B2* | 5/2012 | Liu ...................... A61B 6/4283 378/205 |
| 8,194,823 B2 | 6/2012 | Ohta et al. |
| 8,243,882 B2 | 8/2012 | Jabri et al. |
| 8,243,883 B2 | 8/2012 | Omernick et al. |
| 8,295,439 B2* | 10/2012 | Yonekawa ........... A61B 6/4494 378/116 |
| 8,324,585 B2 | 12/2012 | McBroom et al. |
| 8,396,188 B2 | 3/2013 | Liu et al. |
| 8,461,544 B2 | 6/2013 | Iwakiri et al. |
| 8,546,777 B2 | 10/2013 | Utsunomiya |
| 8,576,986 B2 | 11/2013 | Liu et al. |
| 8,616,766 B2 | 12/2013 | Takahashi et al. |
| 8,618,491 B2 | 12/2013 | Shimizukawa |
| 8,654,925 B2 | 2/2014 | Nishino |
| 8,727,619 B2 | 5/2014 | Yamamichi |
| 8,729,484 B2 | 5/2014 | Nishino et al. |
| 8,786,873 B2 | 7/2014 | Sabol et al. |
| 8,848,872 B2 | 9/2014 | Lee et al. |
| 8,855,691 B2 | 10/2014 | Kamiya et al. |
| 9,118,635 B2 | 8/2015 | Jabri et al. |
| 9,134,436 B2 | 9/2015 | Kwak et al. |
| 9,168,011 B2* | 10/2015 | Nenoki ................. A61B 6/4283 |
| 9,186,118 B2* | 11/2015 | Yonekawa ........... A61B 6/4233 |
| 9,192,350 B2 | 11/2015 | Hiroike |
| 9,195,899 B2 | 11/2015 | Topfer et al. |
| 9,198,270 B2 | 11/2015 | Chicchetti et al. |
| 9,265,476 B2* | 2/2016 | Iwakiri ................. A61B 6/4233 |
| 9,339,246 B2 | 5/2016 | Lemaire et al. |
| 9,402,592 B2 | 8/2016 | Garcia et al. |
| 9,405,183 B2* | 8/2016 | Ando .................... A61B 6/4266 |
| 9,471,980 B2 | 10/2016 | Liu et al. |
| 9,492,137 B2* | 11/2016 | Iwamoto .............. A61B 6/4283 |
| 9,535,176 B2 | 1/2017 | Miyoshi et al. |
| 9,538,978 B2* | 1/2017 | Makino .................. G06F 19/00 |
| 9,655,575 B2* | 5/2017 | Park ..................... A61B 6/4233 |
| 9,661,728 B2* | 5/2017 | Eguchi ..................... H05G 1/08 |
| 9,665,254 B2* | 5/2017 | Hayashi .............. G06F 3/04817 |
| 9,668,706 B2 | 6/2017 | Kim |
| 9,814,435 B2 | 11/2017 | Kim et al. |
| 9,826,948 B2 | 11/2017 | Lee et al. |
| 9,955,931 B2* | 5/2018 | Bettouyashiki ....... A61B 6/4291 |
| 9,968,315 B2* | 5/2018 | Ogura ................... A61B 6/4283 |
| 10,058,297 B2* | 8/2018 | Park ........................ A61B 6/461 |
| 10,076,293 B2 | 9/2018 | Sehnert .................... A61B 6/06 |
| 10,102,620 B2* | 10/2018 | Miyazawa ............ A61B 6/025 |
| 10,206,642 B2* | 2/2019 | Hiroike .................. A61B 6/463 |
| 10,219,766 B2* | 3/2019 | Park ....................... A61B 6/4283 |
| 10,251,619 B2* | 4/2019 | Park ....................... H04W 8/005 |
| 10,271,814 B2* | 4/2019 | Kawanishi ........... A61B 6/4464 |
| 10,327,729 B2* | 6/2019 | Hayashi ................ A61B 6/566 |
| 10,332,280 B2* | 6/2019 | Nishii .................... A61B 6/025 |
| 10,342,508 B2* | 7/2019 | Matsushita .......... A61B 6/4266 |
| 10,383,582 B2* | 8/2019 | Miyazawa ............ A61B 6/5211 |
| 10,441,233 B2* | 10/2019 | Inoue ...................... A61B 6/54 |
| 10,617,304 B2* | 4/2020 | Ohta ...................... A61B 5/0071 |
| 10,667,670 B2* | 6/2020 | Ohta .................... A61B 1/00011 |
| 2004/0258204 A1 | 12/2004 | Nokita et al. |
| 2005/0207534 A1 | 9/2005 | Petrick et al. |
| 2006/0188071 A1 | 8/2006 | Spahn |
| 2006/0285637 A1 | 12/2006 | Varjonen et al. |
| 2008/0049901 A1 | 2/2008 | Tamakoshi |
| 2009/0032745 A1 | 2/2009 | Kito et al. |
| 2009/0130983 A1 | 5/2009 | Venturino et al. |
| 2011/0075817 A1 | 3/2011 | Takahashi et al. |
| 2011/0274244 A1 | 11/2011 | Jabri et al. |
| 2011/0274251 A1 | 11/2011 | Omernick et al. |
| 2012/0195407 A1 | 8/2012 | Nenoki et al. |
| 2012/0207278 A1 | 8/2012 | Yonekawa |
| 2012/0250826 A1 | 10/2012 | Watanabe et al. |
| 2013/0077760 A1 | 3/2013 | Tagawa |

FOREIGN PATENT DOCUMENTS

| | | |
|---|---|---|
| JP | 10-90419 A | 4/1998 |
| JP | 2003-310591 A | 11/2003 |
| JP | 2005-270656 A | 10/2005 |
| JP | 2011-235091 A | 11/2011 |
| JP | 2011-235093 A | 11/2011 |
| JP | 2012-50596 A | 3/2012 |
| JP | 2013-72708 A | 4/2013 |
| KR | 10-2005-0000346 A | 1/2005 |

(56) References Cited

FOREIGN PATENT DOCUMENTS

KR    10-2009-0124927 A    12/2009
KR    10-2012-0093350 A    8/2012

OTHER PUBLICATIONS

Communication dated Mar. 14, 2019 issued by the State Intellectual Property Office of P.R. China in counterpart Chinese Application No. 201480072529.2.
Communication dated Nov. 30, 2016 issued by The Korean Intellectual Property Office in counterpart Korean Application No. 10-2014-0153394.
Communication dated Mar. 18, 2015 issued by European Patent Office in counterpart European Application No. 14192410.0.
International Search Report dated Mar. 12, 2015 issued by International Searching Authority in counterpart International Application No. PCT/KR2014/010721.
Written Opinion dated Mar. 12, 2015 issued by International Searching Authority in counterpart International Application No. PCT/KR2014/010721.
"DRX1 System", Carestream Health Inc., 2012, 4 pages total, www.carestream.com/drx1.
Communication dated May 17, 2016, issued by the Korean Intellectual Property Office in corresponding Korean Application No. 10-2014-0153394.
Communication dated Dec. 19, 2019, issued by the Korean Intellectual Property Office in corresponding Korean Application No. 10-2017-0014077.

* cited by examiner

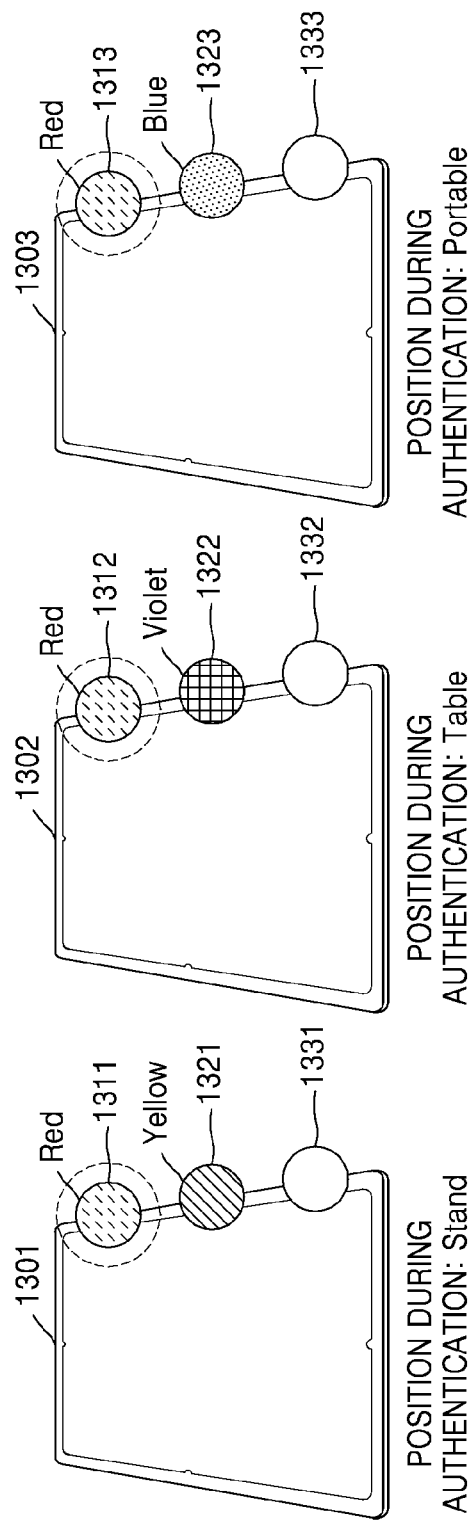

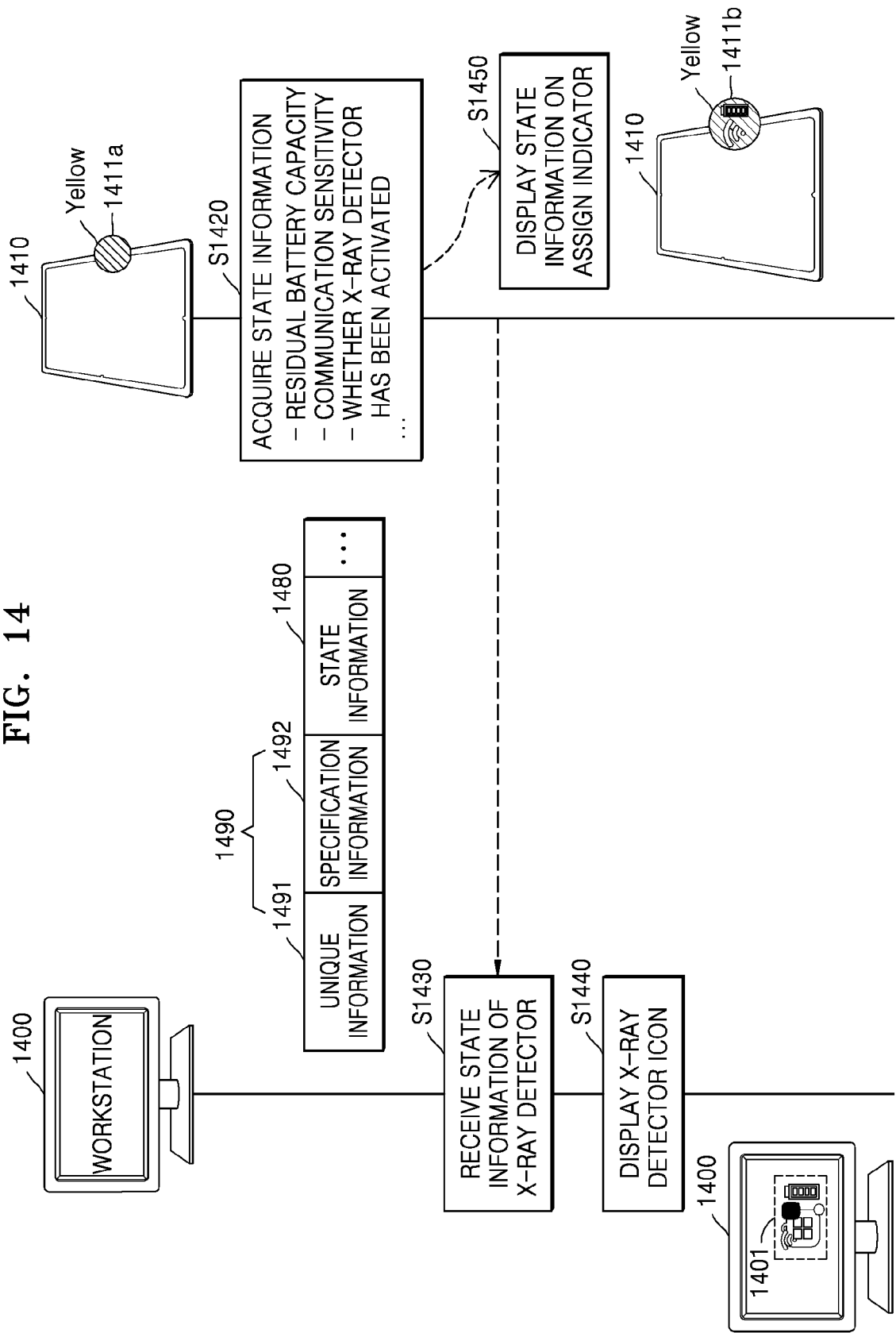

FIG. 17B
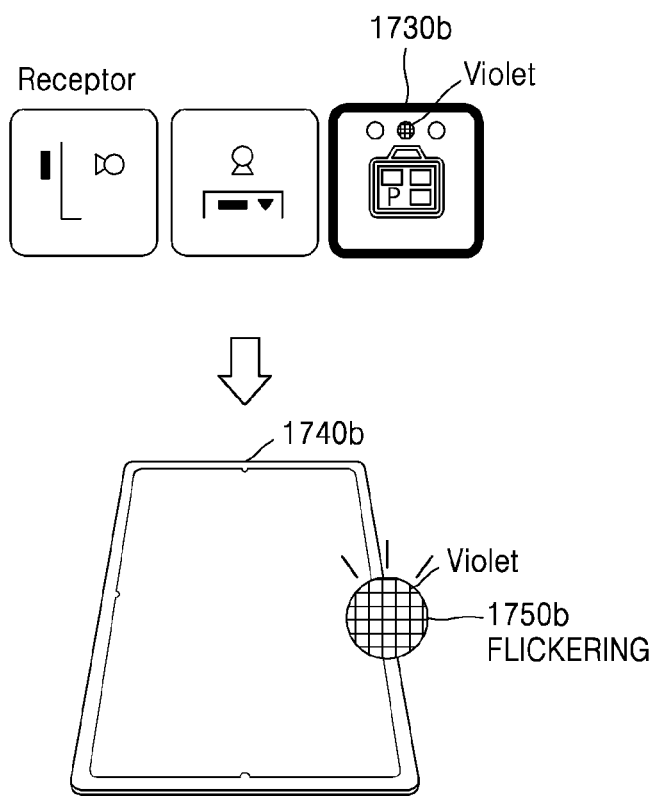
POSITION DURING AUTHENTICATION : Table
CURRENT POSITION : Portable
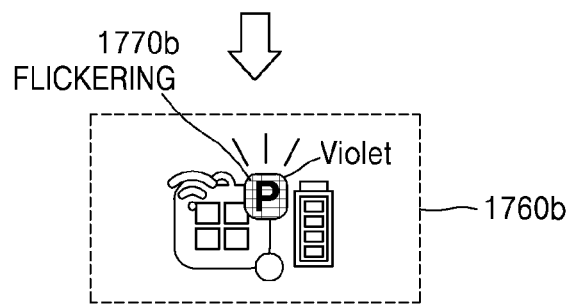

FIG. 17C
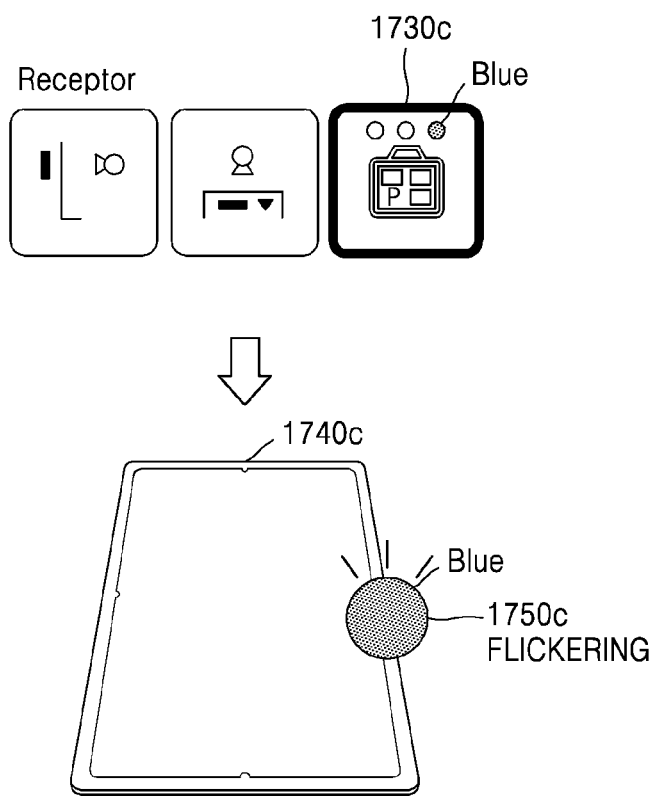
POSITION DURING AUTHENTICATION : Portable
CURRENT POSITION : Portable
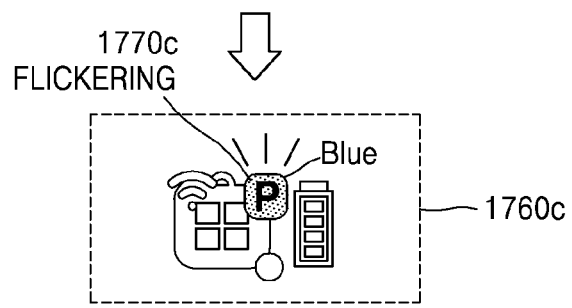

MEDICAL IMAGING SYSTEM AND WORKSTATION AND X-RAY DETECTOR THEREOF

CROSS-REFERENCE TO RELATED APPLICATIONS

This application is a continuation of U.S. application Ser. No. 14/536,775, filed Nov. 10, 2014, which issued as now U.S. Pat. No. 10,058,297 B2 on Aug. 28, 2018, and which claims the benefit of U.S. Provisional Patent Application No. 61/901,692, filed on Nov. 8, 2013, in the U.S. Patent and Trademark Office, and priority from Korean Patent Application No. 2013-0147526, filed on Nov. 29, 2013, and Korean Patent Application No. 2014-0118017, filed on Sep. 4, 2014, and Korean Patent Application No. 2014-0153394, filed on Nov. 6, 2014, in the Korean Intellectual Property Office, the disclosures of which are incorporated herein by reference in their entirety.

BACKGROUND

1. Field

Apparatuses and methods consistent with exemplary embodiments relate to a medical imaging system and workstation and an X-ray detector thereof, and more particularly, to a workstation capable of setting assign indicator information of an X-ray detector, and an X-ray detector capable of displaying an assign indicator.

2. Description of Related Art

In general, X-rays are electromagnetic waves which have a wavelength of 0.01 to 100 Å and which can pass through objects. Thus, they may be commonly used in a wide range of applications, such as medical equipment that take images of the inside of a living body and non-destructive testing equipment for industrial use.

X-ray photographing apparatuses using X-rays allow X-rays emitted by an X-ray tube (or X-ray source) to pass through an object, and detect a difference between the intensities of the passed X-rays by using an X-ray detector to thereby identify the internal structure of the object. X-ray imaging apparatuses are able to easily identify the internal structure of an object by using the principle that the transmission coefficient of X-rays varies depending on the density of the object and the atomic number the atoms of the object. As the wavelength of an X-ray becomes shorter, the transmission coefficient of X-rays increases and a picture on a screen becomes clearer.

SUMMARY

One or more exemplary embodiments include a workstation capable of controlling an assign indicator of an X-ray detector, and an X-ray detector that may be efficiently distinguished from other X-ray detectors by displaying the assign indicator.

Additional aspects will be set forth in part in the description which follows and, in part, will be apparent from the description, or may be learned by practice of the exemplary embodiments.

According to an aspect of an exemplary embodiment, there is provided a workstation including: a receiver configured to receive identification information of an X-ray detector from the X-ray detector; a controller configured to set assign indicator information of the X-ray detector, based on the received identification information of the X-ray detector; an output unit configured to display the set assign indicator information of the X-ray detector; and a transmitter configured to transmit the set assign indicator information of the X-ray detector to the X-ray detector.

The workstation may further include an input unit configured to receive an input for re-setting the set assign indicator information of the X-ray detector. The controller may be further configured to re-set the set assign indicator information in response to the input.

The identification information of the X-ray detector may include at least one selected from unique information including at least one of a serial number (SN) and an Internet Protocol (IP) address of the X-ray detector; and specification information including at least one of a size of the X-ray detector and a type of a receptor with which the X-ray detector is combinable.

The identification information of the X-ray detector may further include position information of the X-ray detector, and the controller may be further configured to authenticate the X-ray detector based on at least one selected from the unique information and the specification information of the X-ray detector, and set assign indicator information of the authenticated X-ray detector, based on the position information of the authenticated X-ray detector.

The position information of the X-ray detector may include at least one selected from information indicating that the X-ray detector has been combined with a stand type receptor, information indicating that the X-ray detector has been combined with a table type receptor, and information indicating that the X-ray detector has not been combined with any receptors.

The identification information of the X-ray detector may further include identification information of a network to which the X-ray detector has been connected, and the controller may be further configured to authenticate the X-ray detector based on at least one selected from the unique information and the specification information of the X-ray detector, and set assign indicator information of the authenticated X-ray detector, based on the identification information of the network to which the authenticated X-ray detector has been connected.

The identification information of the network to which the X-ray detector has been connected may include a service set identifier (SSID) of the network.

The output unit may display an X-ray detector icon that represents the identification information of the X-ray detector and the assign indicator information of the X-ray detector.

The receiver may be further configured to receive state information of the X-ray detector, and the output unit may be further configured to display an X-ray detector icon that represents the state information of the X-ray detector and the assign indicator information of the X-ray detector.

The output unit may be further configured to the X-ray detector icon flicker according to the state information of the X-ray detector.

The state information of the X-ray detector may include at least one selected from information about a residual battery capacity of the X-ray detector, information about a communication sensitivity of the X-ray detector, and information about whether the X-ray detector has been activated.

The receiver and the transmitter may be further configured to communicate with an external apparatus via a wireless network.

The set assign indicator information may include information that indicates at least one selected from a character, a number, a symbol, a color, and an image.

According to an aspect of another exemplary embodiment, there is provided an X-ray detector including: a transmitter configured to transmit identification information of the X-ray detector to a workstation; a receiver configured to receive assign indicator information from the workstation after the transmitter transmits the identification information to the workstation; and an output unit configured to display an assign indicator based on the received assign indicator information.

The receiver may be further configured to receive re-setting information used to reset the displayed assign indicator, and the output unit may be further configured to change the assign indicator based on the received re-setting information and display the changed assign indicator.

The transmitted identification information may include at least one selected from unique information including at least one of a serial number (SN) and an Internet Protocol (IP) address of the X-ray detector, and specification information including at least one of a size of the X-ray detector and a type of a receptor with which the X-ray detector is combinable.

The transmitted identification information may further include position information of the X-ray detector.

The position information of the X-ray detector may include at least one selected from information indicating that the X-ray detector has been combined with a stand type receptor, information indicating that the X-ray detector has been combined with a table type receptor, and information indicating that the X-ray detector has not been combined with any receptors.

The transmitted identification information may further include identification information of a network to which the X-ray detector has been connected.

The identification information of the network to which the X-ray detector has been connected may include a service set identifier (SSID) of the network.

The X-ray detector may further include a controller configured to acquire state information of the X-ray detector. The output unit may be further configured to display the acquired state information of the X-ray detector and the assign indicator.

The acquired state information of the X-ray detector may include at least one selected from information about a residual battery capacity of the X-ray detector, information about a communication sensitivity of the X-ray detector, and information about whether the X-ray detector has been activated.

The output unit may be further configured to make the assign indicator flicker according to the received state information of the X-ray detector.

The receiver and the transmitter may be further configured to communicate with an external apparatus via a wireless network.

The received assign indicator information may include information that indicates at least one selected from a character, a number, a symbol, a color, and an image.

The output unit may include a light source configured to generate light of a color indicated by the assign indicator information; and an optical waveguide which is positioned on at least one edge of the X-ray detector and guides the light to propagate in a certain direction.

The optical waveguide may include a first reflector for guiding the light to propagate in a certain direction within the optical waveguide.

One side of the optical waveguide may include an irregularity for propagating the light to outside of the optical waveguide.

The irregularity formed on the one side of the optical waveguide may be repeated, and a repetition interval of the irregularity may shorten in a direction away from the light source.

The X-ray detector may further include a second reflector which is positioned on one side of the optical waveguide and propagates the light to outside of the optical waveguide.

According to an aspect of another exemplary embodiment, there is provided an X-ray apparatus including: an X-ray radiation unit configured to radiate an X-ray to an object; and a manipulation unit configured to manipulate the X-ray radiation unit. The manipulation unit may include: a receiver configured to receive identification information of an X-ray detector from the X-ray detector; a controller configured to set assign indicator information of the X-ray detector, based on the received identification information of the X-ray detector; an output unit configured to display the set assign indicator information of the X-ray detector; and a transmitter configured to transmit the set assign indicator information of the X-ray detector to the X-ray detector.

According to an aspect of another exemplary embodiment, there is provided an X-ray system including: an X-ray apparatus including an X-ray radiation unit and an X-ray detector; and a workstation configured to control the X-ray apparatus.

The workstation may include a receiver configured to receive identification information of the X-ray detector from the X-ray detector; a controller configured to set assign indicator information of the X-ray detector, based on the received identification information of the X-ray detector; an output unit configured to display the set assign indicator information of the X-ray detector; and a transmitter configured to transmit the set assign indicator information of the X-ray detector to the X-ray detector.

The X-ray detector may include a transmitter configured to transmit identification information of the X-ray detector to the workstation; a receiver configured to receive assign indicator information from the workstation after the transmitter transmits the identification information of the X-ray detector to the workstation; and an output unit configured to display an assign indicator based on the received assign indicator information.

According to an aspect of another exemplary embodiment, there is provided a method of capturing an X-ray image including: setting assign indicator information of an X-ray detector, based on identification information of the X-ray detector; displaying an assign indicator on the X-ray detector, based on the set assign indicator information of the X-ray detector; and capturing the X-ray image by using the X-ray detector on which the assign indicator has been displayed.

BRIEF DESCRIPTION OF THE DRAWINGS

The above and/or other aspects will become apparent and more readily appreciated from the following description of the exemplary embodiments, taken in conjunction with the accompanying drawings in which:

FIG. 13 illustrates respective operations of X-ray detectors according to the assign indicator information of FIG. 12;

FIG. 14 is a diagram for describing respective operations of a workstation and an X-ray detector according to another exemplary embodiment;

FIGS. 17A-18B illustrate an operation in which the workstation of FIG. 6 activates an X-ray detector, according to one or more exemplary embodiments;

DETAILED DESCRIPTION

Figure 1:
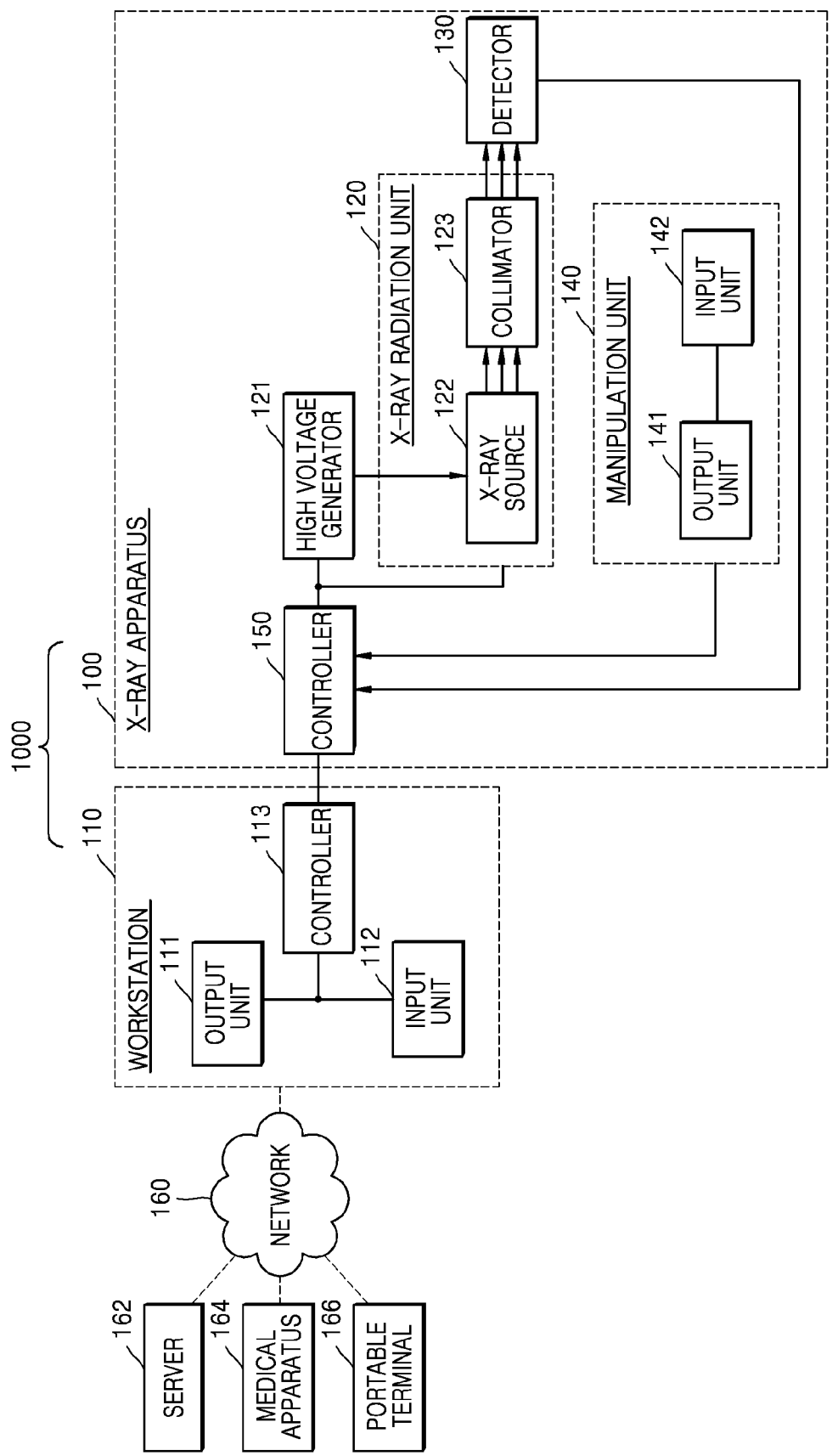
FIG. 1 is a block diagram of an X-ray system.

Certain exemplary embodiments will now be described in greater detail with reference to the accompanying drawings. The matters defined in the specification, such as detailed construction and elements, are provided to assist in a comprehensive understanding of the exemplary embodiments. The invention may, however, be embodied in many different forms and should not be construed as being limited to the exemplary embodiments set forth herein; rather, these exemplary embodiments are provided so that this disclosure will be thorough and complete, and will fully convey the concept of the invention to those skilled in the art, the scope of which is defined by the appended claims. Also, well known functions or constructions are not described in detail since they would obscure the exemplary embodiments with unnecessary detail.

Hereinafter, the terms used in the specification will be briefly described, and then the exemplary embodiments will be described in detail.

Although certain general terms widely used at present were selected for describing the exemplary embodiments in consideration of the functions thereof, these general terms may vary according to intentions of one of ordinary skill in the art, case precedents, the advent of new technologies, and the like. Terms arbitrarily selected by the applicant of the exemplary embodiments may also be used in a specific case. In this case, their meanings are given in the detailed description of the exemplary embodiments. Hence, these terms are defined based on their meanings and the contents of the entire specification, not by simply stating the terms.

Throughout the specification, an "image" may refer to multi-dimensional data formed of discrete image elements (e.g., pixels in a two-dimensional (2D) image and voxels in a three-dimensional (3D) image). For example, an image may be a medical image of an object acquired by an X-ray apparatus, a computed tomography (CT) apparatus, a magnetic resonance imaging (MRI) apparatus, an ultrasound diagnosis apparatus, or another medical imaging apparatus.

In addition, an "object" may be a human, an animal, or a part of a human or animal. For example, the object may include an organ (for example, the liver, the heart, the womb, the brain, breasts, or the abdomen), blood vessels, or a combination thereof. The object may be a phantom. The phantom denotes a material having a volume, a density, and an effective atomic number that are approximately the same as those of a living organism. For example, the phantom may be a spherical phantom having similar properties to those of the human body.

Furthermore, a "user" may be, but is not limited to, a medical expert, for example, a medical doctor, a nurse, a medical laboratory technologist, or a medical imaging expert, or a technician who repairs medical apparatuses.

An X-ray apparatus is a medical imaging apparatus that acquires images of internal structures of an object by transmitting an X-ray through the human body. The X-ray apparatus may acquire medical images of an object more simply and within a shorter time than other medical imaging apparatuses including an MRI apparatus and a CT apparatus. Therefore, the X-ray apparatus is widely used in simple chest photographing, simple abdomen photographing, simple skeleton photographing, simple nasal sinuses photographing, simple neck soft tissue photographing, breast photographing, etc.

FIG. 1 is a block diagram of an X-ray system 1000.

Referring to FIG. 1, the X-ray system 1000 includes an X-ray apparatus 100 and a workstation 110. The X-ray apparatus 100 shown in FIG. 1 may be a fixed-type X-ray apparatus or a mobile X-ray apparatus. The X-ray apparatus 100 may include an X-ray radiation unit 120, a high voltage generator 121, a detector 130, a manipulation unit 140, and a controller 150. The controller 150 may control overall operations of the X-ray apparatus 100.

The high voltage generator 121 generates a high voltage for generating X-rays, and applies the high voltage to an X-ray source 122.

The X-ray radiation unit 120 includes the X-ray source 122 receiving the high voltage from the high voltage generator 121 to generate and radiate X-rays, and a collimator 123 for guiding a path of the X-ray radiated from the X-ray source 122 and adjusting an irradiation region radiated by the X-ray.

The X-ray source 122 includes an X-ray tube that may be realized as a vacuum tube diode including a cathode and an anode. An inside of the X-ray tube may be set as a high vacuum state of about 10 mmHg, and a filament of the anode is heated to a high temperature to generate thermal electrons. The filament may be a tungsten filament, and a voltage of about 10V and a current of about 3 to 5 A may be applied to an electric wire connected to the filament to heat the filament.

In addition, when a high voltage of about 10 to about 300 kVp is applied between the cathode and the anode, the thermal electrons are accelerated to collide with a target material of the cathode, and then, an X-ray is generated. The X-ray is radiated to the outside via a window, and the window may be formed of a beryllium thin film. In this case, most of the energy of the electrons colliding with the target material is consumed as heat, and remaining energy is converted into the X-ray.

The cathode may be mainly formed of copper, and the target material is disposed opposite to the anode. The target material may be a high resistive material such as chromium (Cr), iron (Fe), cobalt (Co), nickel (Ni), tungsten (W), or molybdenum (Mo). The target material may be rotated by a rotating field. When the target material is rotated, an electron impact area is increased, and a heat accumulation rate per unit area may be increased to be at least ten times greater than that of a case where the target material is fixed.

The voltage applied between the cathode and the anode of the X-ray tube is referred to as a tube voltage, and the tube voltage is applied from the high voltage generator 121 and a magnitude of the tube voltage may be expressed by a crest value (kVp). When the tube voltage increases, a velocity of the thermal electrons increases, and accordingly, an energy of the X-ray (that is, energy of the photons) that is generated when the thermal electrons collide with the target material is increased. The current flowing in the X-ray tube is referred to as a tube current that may be expressed as an average value (mA). When the tube current increases, the number of thermal electrons emitted from the filament is increased, and accordingly, the X-ray dose (that is, the number of X-ray photons) generated when the thermal electrons collide with the target material is increased.

Therefore, the energy of the X-ray may be adjusted according to the tube voltage, and the intensity of the X-ray or the X-ray dose may be adjusted according to the tube current and the X-ray exposure time.

The detector 130 detects an X-ray that is radiated from the X-ray radiation unit 120 and has been transmitted through an object. The detector 130 may be a digital detector. The detector 130 may be implemented by using a thin film transistor (TFT) or a charge coupled device (CCD). Although the detector 130 is included in the X-ray apparatus 100 in FIG. 1, the detector 130 may be an X-ray detector that is a separate device capable of being connected to or separated from the X-ray apparatus 100.

The X-ray apparatus 100 may further include a manipulation unit 140 for providing a user with an interface for manipulating the X-ray apparatus 100. The manipulation unit 140 may include an output unit 141 and an input unit 142. The input unit 142 may receive, from a user, a command for manipulating the X-ray apparatus 100 and various types of information related to X-ray photographing. The controller 150 may control or manipulate the X-ray apparatus 100 according to the information received by the input unit 142. The output unit 141 may output sound representing information related to a photographing operation such as the X-ray radiation under the control of the controller 150.

The workstation 110 and the X-ray apparatus 100 may be connected to each other by wire or wirelessly. When they are connected to each other wirelessly, a device (not shown) for synchronizing clock signals with each other may be further included. The workstation 110 and the X-ray apparatus 100 may exist within physically separate spaces.

The workstation 110 may include an output unit 111, an input unit 112, and a controller 113. The output unit 111 and the input unit 112 provide a user with an interface for manipulating the workstation 110 and the X-ray apparatus 100. The controller 113 may control the workstation 110 and the X-ray apparatus 100.

The X-ray apparatus 100 may be controlled via the workstation 110 or may be controlled by the controller 150 included in the X-ray apparatus 100. Accordingly, a user may control the X-ray apparatus 100 via the workstation 110 or may control the X-ray apparatus 100 via the manipulation unit 140 and the controller 150 included in the X-ray apparatus 100. In other words, a user may remotely control the X-ray apparatus 100 via the workstation 110 or may directly control the X-ray apparatus 100.

Although the controller 113 of the workstation 110 is separate from the controller 150 of the X-ray apparatus 100 in FIG. 1, FIG. 1 is only an example. As another example, the controllers 113 and 150 may be integrated into a single controller, and the single controller may be included in only one of the workstation 110 and the X-ray apparatus 100. Hereinafter, the controllers 113 and 150 may denote the controller 113 of the workstation 110 and/or the controller 150 of the X-ray apparatus 100.

The output unit 111 and the input unit 112 of the workstation 110 may provide a user with an interface for manipulating the X-ray apparatus 100, and the output unit 141 and the input unit 142 of the X-ray apparatus 100 may also provide a user with an interface for manipulating the X-ray apparatus 100. Although the workstation 110 and the X-ray radiation unit 100 include the output units 111 and 141, respectively, and the input units 112 and 142, respectively, in FIG. 1, exemplary embodiments are not limited thereto. For example, only one of the workstation 110 and the X-ray apparatus 100 may include an output unit or an input unit.

Hereinafter, the input units 112 and 142 may denote the input unit 112 of the workstation 110 and/or the input unit 142 of the X-ray apparatus 100, and the output units 111 and 141 may denote the output unit 111 of the workstation 110 and/or the output unit 141 of the X-ray apparatus 100.

Examples of the input units 112 and 142 may include a keyboard, a mouse, a touch screen, a voice recognizer, a fingerprint recognizer, an iris recognizer, and other input devices which are well known to one of ordinary skill in the art and will not be described in further detail. The user may input a command for radiating the X-ray via the input units 112 and 142, and the input units 112 and 142 may include a switch for inputting the command. The switch may be configured so that a radiation command for radiating the X-ray may be input only when the switch is pushed twice.

In other words, when the user pushes the switch, a prepare command for performing a pre-heating operation for X-ray radiation may be input through the switch, and then, when the user pushes the switch once more, the radiation command for performing substantial X-ray radiation may be input through the switch. When the user manipulates the switch as described above, the controllers 113 and 150 generate signals corresponding to the commands input through the switch manipulation, that is, a prepare signal, and transmit the generated signals to the high voltage generator 121 generating a high voltage for generating the X-ray.

When the high voltage generator 121 receives the prepare signal from the controllers 113 and 150, the high voltage generator 121 starts a pre-heating operation, and when the pre-heating is finished, the high voltage generator 121 outputs a ready signal to the controllers 113 and 150. In addition, as the detector 130 also needs to prepare to detect the X-ray, when the high voltage generator 121 performs the pre-heating operation, and controllers 113 and 150 transmit a prepare signal to the detector 130 so that the detector 130 may prepare to detect the X-ray transmitted through the object. The detector 130 prepares to detect the X-ray in response to the prepare signal, and when the preparing for the detection is finished, the detector 130 transmits a ready signal to the controllers 113 and 150. The preparing for the detection by the detector 130 may be referred to as "activation" or the like.

When the pre-heating operation of the high voltage generator 121 is finished and the detector 130 is ready to detect the X-ray, the controllers 113 and 150 transmit a radiation signal to the high voltage generator 121, the high voltage generator 121 generates and applies the high voltage to the X-ray source 122, and the X-ray source 122 radiates the X-ray.

When the controllers 113 and 150 transmit the radiation signal to the high voltage generator 121, the controllers 113 and 150 may transmit a sound output signal to the output units 111 and 141 so that the output units 111 and 141 output a predetermined sound so that the user and/or the object (for example, a patent being X-rayed) may recognize the radiation of the X-ray. The output units 111 and 141 may also output a sound representing information related to photographing in addition to the X-ray radiation. In FIG. 1, the output unit 141 is included in the manipulation unit 140; however, the exemplary embodiments are not limited thereto, and the output unit 141 or a portion of the output unit 141 may be located elsewhere. For example, the output unit 141 may be located on a wall of an examination room in which the X-ray photographing of the object is performed.

The controllers 113 and 150 control locations of the X-ray radiation unit 120 and the detector 130, photographing timing, and photographing conditions, according to photographing conditions set by the user.

In more detail, the controllers 113 and 150 control the high voltage generator 121 and the detector 130 according to the command input via the input units 112 and 142 so as to control radiation timing of the X-ray, an intensity of the X-ray, and a region irradiated by the X-ray. In addition, the controllers 113 and 150 adjust the location of the detector 130 according to a predetermined photographing condition, and controls operation timing of the detector 130.

Furthermore, the controllers 113 and 150 generate a medical image of the object by using image data received via the detector 130. In detail, the controllers 113 and 150 may receive the image data from the detector 130, and then, generate the medical image of the object by removing noise from the image data and adjusting a dynamic range and interleaving of the image data.

The output units 111 and 141 may output the medical image generated by the controllers 113 and 150. The output units 111 and 141 may output information that is necessary for the user to manipulate the X-ray apparatus 100, for example, a user interface (UI), user information, or object information. Examples of the output units 111 and 141 may include a speaker, a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a flat panel display (FPD), a three-dimensional (3D) display, a transparent display, and other various output devices well known to one of ordinary skill in the art.

The workstation 110 shown in FIG. 1 may further include a communication unit (not shown) that may be connected to a server 162, a medical apparatus 164, and a portable terminal 166 via a network 160.

The communication unit may be connected to the network 160 by wire or wirelessly to communicate with the external server 162, the external medical apparatus 164, or the external portable terminal 166. The communication unit may transmit or receive data related to diagnosis of the object via the network 160, and may also transmit or receive medical images captured by the medical apparatus 164, for example, a CT apparatus, an MRI apparatus, or an X-ray apparatus. Moreover, the communication unit may receive a medical history or treatment schedule of an object (e.g., a patient) from the server 162 to diagnose a disease of the object. Furthermore, the communication unit may perform data communication with the portable terminal 166 such as a mobile phone, a personal digital assistant (PDA), or a laptop computer of a medical doctor or a client, as well as the server 162 or the medical apparatus 164 in a hospital.

The communication unit may include one or more elements enabling communication with external apparatuses. For example, the communication unit may include a short distance communication module, a wired communication module, and a wireless communication module.

The short distance communication module refers to a module for performing short distance communication with an apparatus located within a predetermined distance. Examples of short distance communication technology may include, but are not limited to, a wireless local area network (LAN), Wi-Fi, Bluetooth, ZigBee, Wi-Fi Direct (WFD), ultra wideband (UWD), infrared data association (IrDA), Bluetooth low energy (BLE), and near field communication (NFC).

The wired communication module refers to a module for communicating by using an electric signal or an optical signal. Examples of wired communication technology may include wired communication techniques using a pair cable, a coaxial cable, and an optical fiber cable, and other wired communication techniques that are well known to one of ordinary skill in the art.

The wireless communication module transmits and receives a wireless signal to and from at least one selected from a base station, an external apparatus, and a server in a mobile communication network. Here, examples of the wireless signal may include a voice call signal, a video call signal, and various types of data according to text/multimedia messages transmission.

The X-ray apparatus 100 shown in FIG. 1 may include a plurality of digital signal processors (DSPs), an ultra-small calculator, and a processing circuit for special purposes (for example, high speed analog/digital (A/D) conversion, high speed Fourier transformation, and an array process).

In addition, communication between the workstation 110 and the X-ray apparatus 100 may be performed using a high speed digital interface, such as low voltage differential signaling (LVDS), asynchronous serial communication, such as a universal asynchronous receiver transmitter (UART), a low latency network protocol, such as error synchronous serial communication or a controller area network (CAN), or any of other various communication methods that are well known to one of ordinary skill in the art.

Figure 2:
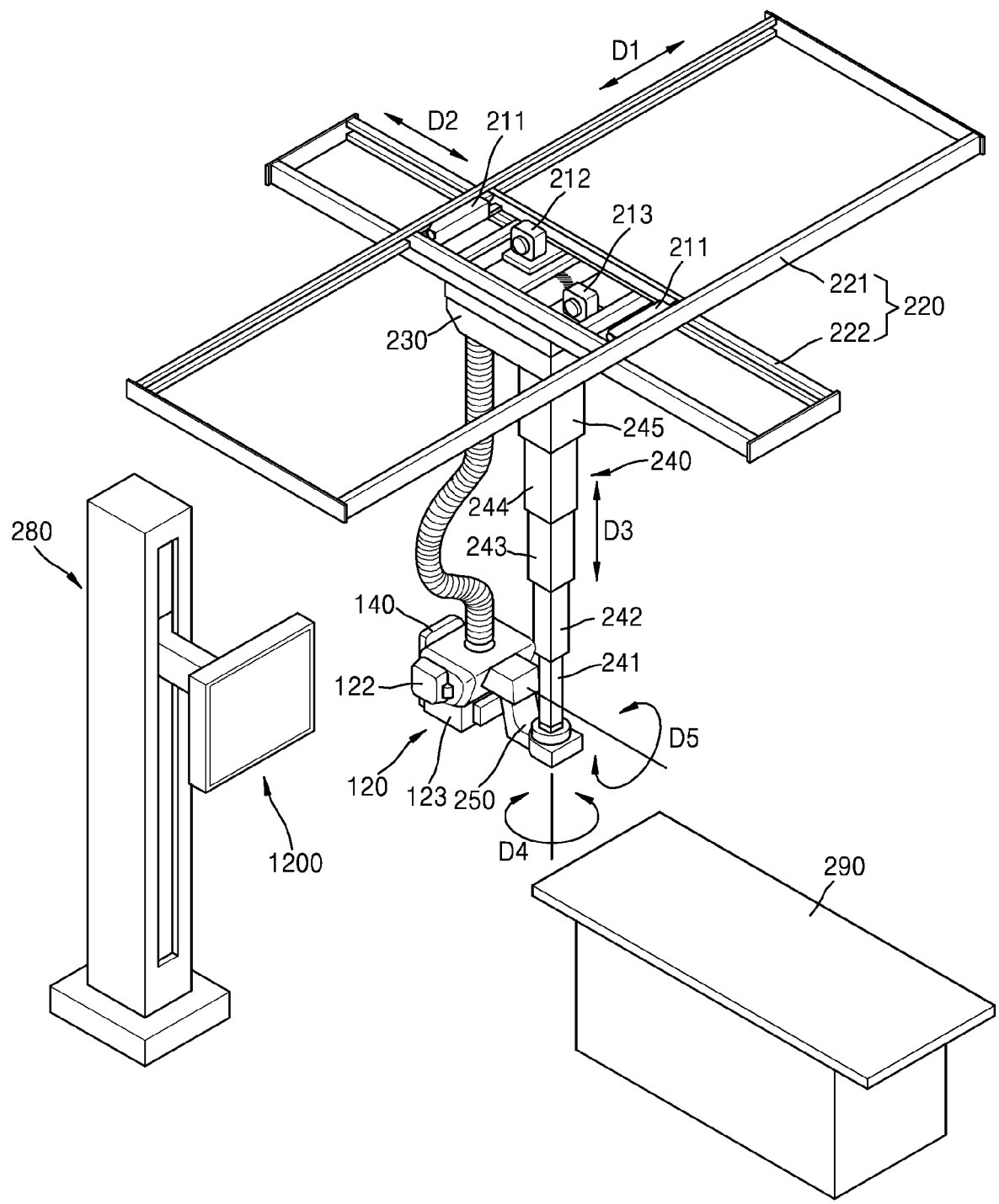
FIG. 2 is a perspective view of a fixed type X-ray apparatus.

FIG. 2 is a perspective view of a fixed type X-ray apparatus 200. The fixed type X-ray apparatus 200 may be another embodiment of the X-ray apparatus 100 of FIG. 1. Components included in the fixed type X-ray apparatus 200 that are the same as those of the X-ray apparatus 100 of FIG. 1 use the same reference numerals, and repeated descriptions thereof will be omitted.

Referring to FIG. 2, the fixed type X-ray apparatus 200 includes a manipulation unit 140 providing a user with an interface for manipulating the X-ray apparatus 200, an X-ray radiation unit 120 radiating an X-ray to an object, a detector 130 detecting an X-ray that has passed through the object, first, second, and third motors 211, 212, and 213 providing a driving power to transport the X-ray radiation unit 120, a guide rail 220, a moving carriage 230, and a post frame 240. The guide rail 220, the moving carriage 230, and the post frame 240 are formed to transport the X-ray radiation unit 120 by using the driving power of the first, second, and third motors 211, 212, and 213.

The guide rail 220 includes a first guide rail 221 and a second guide rail 222 that are provided to form a predetermined angle with respect to each other. The first guide rail 221 and the second guide rail 222 may respectively extend in directions crossing each other at 90° (that is, perpendicular).

The first guide rail 221 may be provided on the ceiling of an examination room in which the X-ray apparatus 200 is disposed.

The second guide rail 222 is located under the first guide rail 221, and is mounted so as to slide along the first guide rail 221. A roller (not shown) that may move along the first guide rail 221 may be provided on the first guide rail 221. The second guide rail 222 is connected to the roller to move along the first guide rail 221.

A first direction D1 is defined as a direction in which the first guide rail 221 extends, and a second direction D2 is defined as a direction in which the second guide rail 222 extends. Therefore, the first direction D1 and the second direction D2 cross each other at 90°, and may be parallel to the ceiling of the examination room.

The moving carriage 230 is disposed under the second guide rail 222 so as to move along the second guide rail 222. A roller (not shown) moving along the second guide rail 222 may be provided on the moving carriage 230.

Therefore, the moving carriage 230 may move in the first direction D1 together with the second guide rail 222, and may move in the second direction D2 along the second guide rail 222.

The post frame 240 is fixed on the moving carriage 230 and located under the moving carriage 230. The post frame 240 may include a plurality of posts 241, 242, 243, 244, and 245.

The plurality of posts 241, 242, 243, 244, and 245 are connected to each other to be foldable, and thus, the post frame 240 may have a length that is adjustable in a vertical direction of the examination room while in a state of being fixed to the moving carriage 230.

A third direction D3 is defined as a direction in which the length of the post frame 240 increases or decreases. Therefore, the third direction D3 may be perpendicular to the first direction D1 and the second direction D2.

The detector 130 detects the X-ray that has passed through the object, and may be combined with a table type receptor 290 or a stand type receptor 280.

A rotating joint 250 is disposed between the X-ray radiation unit 120 and the post frame 240. The rotating joint 250 allows the X-ray radiation unit 120 to be coupled to the post frame 240, and supports a load applied to the X-ray radiation unit 120.

The X-ray radiation unit 120 connected to the rotating joint 250 may rotate on a plane that is perpendicular to the third direction D3. In this case, a rotating direction of the X-ray radiation unit 120 may be defined as a fourth direction D4.

The X-ray radiation unit 120 may be configured to be rotatable on a plane perpendicular to the ceiling of the examination room. Therefore, the X-ray radiation unit 120 may rotate in a fifth direction D5 that is a rotating direction about an axis that is parallel with the first direction D1 or the second direction D2, with respect to the rotating joint 250.

The first, second, and third motors 211, 212, and 213 may be provided to move the X-ray radiation unit 120 in the first, second, and third directions D1, D2, and D3. The first, second, and third motors 211, 212, and 213 may be electrically driven, and the first, second, and third motors 211, 212, and 213 may respectively include an encoder.

The first, second, and third motors 211, 212, and 213 may be disposed at various locations in consideration of design convenience. For example, the first motor 211, moving the second guide rail 222 in the first direction D1, may be disposed around the first guide rail 221, the second motor 212, moving the moving carriage 230 in the second direction D2, may be disposed around the second guide rail 222, and the third motor 213, increasing or reducing the length of the post frame 240 in the third direction D3, may be disposed in the moving carriage 230. In another example, the first, second, and third motors 211, 212, and 213 may be connected to a power transfer unit (not shown) so as to linearly move the X-ray radiation unit 120 in the first, second, and third directions D1, D2, and D3. The driving power transfer unit may be a combination of a belt and a pulley, a combination of a chain and a sprocket, a shaft, etc. which are generally used and will not be described in detail.

In another example, motors (not shown) may be disposed between the rotating joint 250 and the post frame 240 and between the rotating joint 250 and the X-ray radiation unit 120 in order to rotate the X-ray radiation unit 120 in the fourth and fifth directions D4 and D5.

The manipulation unit 140 may be disposed on a side surface of the X-ray radiation unit 120.

Although FIG. 2 shows the fixed type X-ray apparatus 200 connected to the ceiling of the examination room, the fixed type X-ray apparatus 200 is merely an example for convenience of comprehension. That is, X-ray apparatuses according to exemplary embodiments may include X-ray apparatuses having various structures that are well known to one of ordinary skill in the art, for example, a C-arm-type X-ray apparatus and an angiography X-ray apparatus, in addition to the fixed type X-ray apparatus 200 of FIG. 2.

Figure 3:
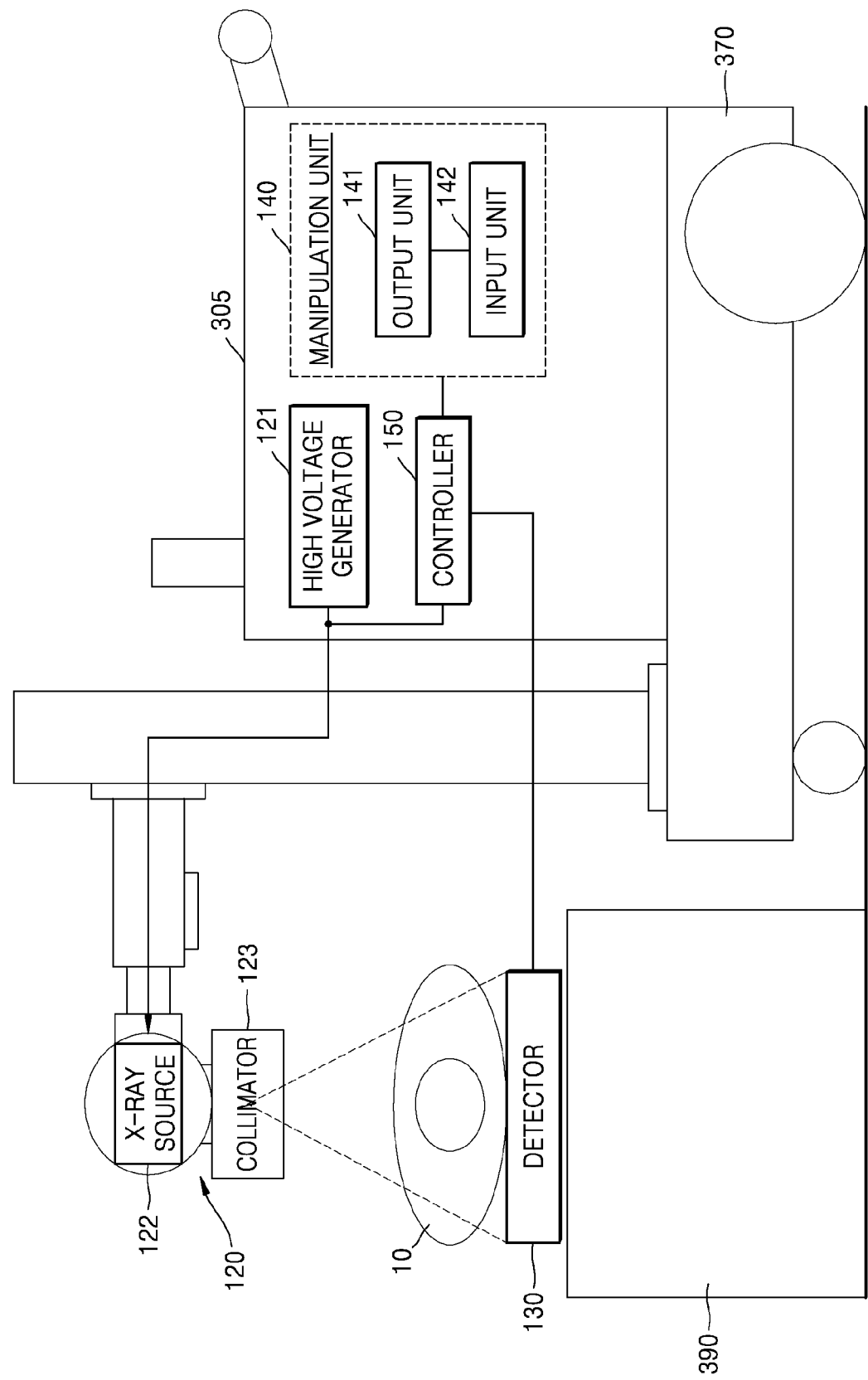
FIG. 3 is a diagram showing a configuration of a mobile X-ray apparatus capable of performing an X-ray photographing operation regardless of a place where the photographing operation is performed.

FIG. 3 is a diagram showing a configuration of a mobile X-ray apparatus 300 capable of performing an X-ray photographing operation regardless of a place where the photographing operation is performed. The mobile X-ray apparatus 300 may be another embodiment of the X-ray apparatus 100 of FIG. 1. Components included in the mobile X-ray apparatus 300 that are the same as those of the X-ray apparatus 100 of FIG. 1 use the same reference numerals as those used in FIG. 1, and a repeated description thereof will be omitted.

Referring to FIG. 3, the mobile X-ray apparatus 300 includes a transport unit 370 including wheels for transporting the mobile X-ray apparatus 300, a main unit 305, an X-ray radiation unit 120, and a detector 130 detecting an X-ray that is radiated from the X-ray radiation unit 120 toward an object and transmitted through the object. The main unit 305 includes a manipulation unit 140 providing a user with an interface for manipulating the mobile X-ray apparatus 300, a high voltage generator 121 generating a high voltage applied to an X-ray source 122, and a controller 150 controlling overall operations of the mobile X-ray apparatus 300. The X-ray radiation unit 120 includes the X-ray source 122 generating the X-ray, and a collimator 123 guiding a path along which the generated X-ray is emitted from the X-ray source 355 and adjusting an irradiation region radiated by the X-ray.

Although the detector 130 is combined with a table type receptor 390 in FIG. 3, the detector 130 may also be combined with a stand type receptor.

In FIG. 3, the manipulation unit 140 is included in the main unit 305; however, exemplary embodiments are not limited thereto. For example, the manipulation unit 140 of the mobile X-ray apparatus 300 may be disposed on a side surface of the X-ray radiation unit 120.

Figure 4:
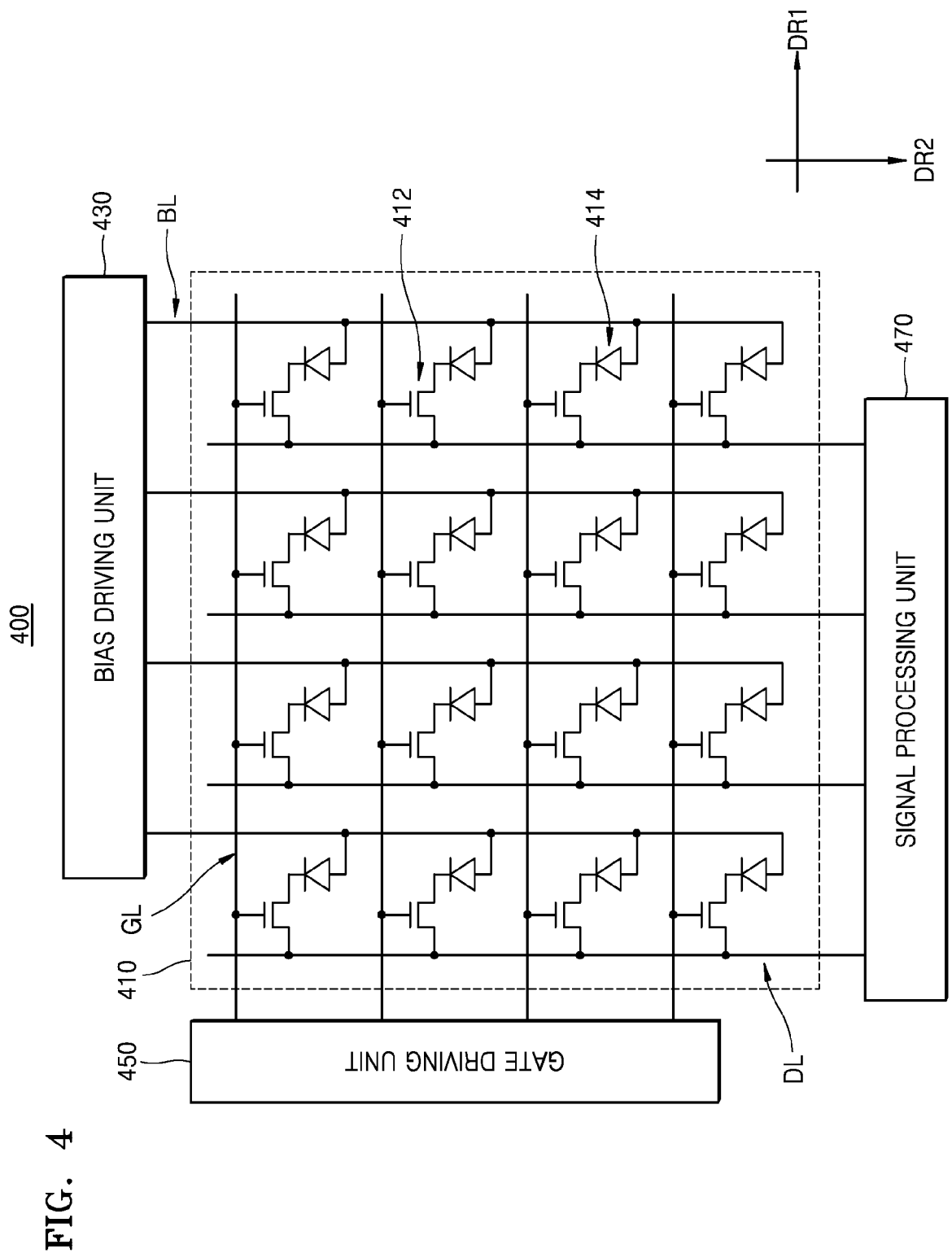
FIG. 4 is a diagram showing a detailed configuration of an indirect type detector.

FIG. 4 is a schematic diagram showing a detailed configuration of a detector 400. The detector 400 may be an embodiment of the detector 130 of FIGS. 1-3. The detector 400 may be an indirect type detector.

Referring to FIG. 4, the detector 400 may include a scintillator (not shown), a photodetecting substrate 410, a bias driving unit 430, a gate driving unit 450, and a signal processing unit 470.

The scintillator receives the X-ray radiated from the X-ray source 122 and converts the X-ray into light.

The photodetecting substrate 410 receives the light from the scitillator and converts the light into an electrical signal. The photodetecting substrate 410 may include gate lines GL, data lines DL, TFTs 412, photodiodes 414, and bias lines BL.

The gate lines GL may be formed in a first direction DR1, and the data lines DL may be formed in a second direction DR2 that crosses the first direction DR1. The first direction DR1 and the second direction DR2 may intersect perpendicularly to each other. FIG. 4 shows four gate lines GL and four data lines DL as an example.

The TFTs 412 may be arranged as a matrix in the first and second directions DR1 and DR2. Each of the TFTs 412 may be electrically connected to one of the gate lines GL and one of the data lines DL. A gate of the TFT 412 may be electrically connected to the gate line GL, and a source of the TFT 412 may be electrically connected to the data line DL. In FIG. 4, sixteen TFTs 412 (in a 4×4 arrangement) are shown as an example.

The photodiodes 414 may be arranged as a matrix in the first and second directions DR1 and DR2 so as to respectively correspond to the TFTs 412. Each of the photodiodes 414 may be electrically connected to one of the TFTs 412. An N-side electrode of each of the photodiodes 414 may be electrically connected to a drain of the TFT 412. FIG. 4 shows sixteen photodiodes 414 (in a 4×4 arrangement) as an example.

The bias lines BL are electrically connected to the photodiodes 414. Each of the bias lines BL may be electrically connected to P-side electrodes of an array of photodiodes 414. For example, the bias lines BL may be formed to be substantially parallel with the second direction DR2 so as to be electrically connected to the photodiodes 414. On the other hand, the bias lines BL may be formed to be substantially parallel with the first direction DR1 so as to be electrically connected to the photodiodes 414. FIG. 4 shows four bias lines BL formed along the second direction DR2 as an example.

The bias driving unit 430 is electrically connected to the bias lines BL so as to apply a driving voltage to the bias lines BL. The bias driving unit 430 may selectively apply a reverse bias voltage or a forward bias voltage to the photodiodes 414. A reference voltage may be applied to the N-side electrodes of the photodiodes 414. The reference voltage may be applied via the signal processing unit 470. The bias driving unit 430 may apply a voltage that is less than the reference voltage to the P-side electrodes of the photodiodes 414 so as to apply a reverse bias voltage to the photodiodes 414. On the other hand, the bias driving unit 430 may apply a voltage that is greater than the reference voltage to the P-side electrodes of the photodiodes 414 so as to apply a forward bias voltage to the photodiodes 414.

The gate driving unit 450 is electrically connected to the gate lines GL and thus may apply gate signals to the gate lines GL. For example, when the gate signals are applied to the gate lines GL, the TFTs 412 may be turned on by the gate signals. On the other hand, when the gate signals are not applied to the gate lines GL, the TFTs 412 may be turned off.

The signal processing unit 470 is electrically connected to the data lines DL. When the light received by the photodetecting substrate 410 is converted into the electrical signal, the electrical signal may be read out by the signal processing unit 470 via the data lines DL.

An operation of the detector 400 will now be described. During the operation of the detector 400, the bias driving unit 430 may apply the reverse bias voltage to the photodiodes 414.

While the TFTs 412 are turned off, each of the photodiodes 414 may receive the light from the scintillator and generate electron-hole pairs to accumulate electric charges. The amount of electric charge accumulated in each of the photodiodes 414 may correspond to the intensity of the received X-ray light.

Then, the gate driving unit 450 may sequentially apply the gate signals to the gate lines GL along the second direction DR2. When a gate signal is applied to a gate line GL and thus TFTs 412 connected to the gate line GL are turned on, photocurrents may flow into the signal processing unit 470 via the data lines DL due to the electric charges accumulated in the photodiodes 414 connected to the turned-on TFTs 412.

The signal processing unit 470 may convert the received photocurrents into image data and output the image data to the outside. The image data may be in the form of an analog signal or a digital signal corresponding to the photocurrents.

Although not shown in FIG. 4, if the detector 400 shown in FIG. 4 is a wireless detector, the detector 400 may further include a battery unit and a wireless communication interface unit.

As described above, the detection unit 130 may be an X-ray detector which is a separate device capable of being connected to or separated from the X-ray apparatus 100. In detail, the X-ray detector may be physically connected to or separated from the X-ray apparatus 100 and may communicate with the X-ray apparatus 100 via a wired or wireless network.

A wired X-ray detector is coupled to the stand type receptor 280 or the table type receptor 290 and thus is not freely movable. On the other hand, a wireless X-ray detector may be coupled to a receptor or may not be coupled to a receptor.

In detail, a wireless X-ray detector may communicate with the X-ray apparatus 100 or the X-ray system 1000 via a wireless network. Accordingly, a user may use a wireless X-ray detector in various locations according to parts of an object to be photographed, without being coupled to a receptor.

Since the wireless X-ray detector is not dependent upon specification information about the receptor, wireless X-ray detectors having various sizes and shapes may be used in an identical X-ray apparatus or an identical X-ray system. The sizes and shapes of X-ray detectors suitable for X-ray imaging may differ according to parts of an object to be photographed.

Thus, a plurality of X-ray detectors of an identical type or of different types may exist in a single X-ray imaging room, and a user needs to select an X-ray detector suitable for a part of an object to be photographed and an imaging environment from among the plurality of X-ray detectors. However, when a plurality of X-ray detectors of an identical type or of different types exist in a single X-ray imaging room, it may be confusing to distinguish the plurality of X-ray detectors from one another or select an X-ray detector that is to be used in X-ray imaging from among the plurality of X-ray detectors.

Therefore, an X-ray detector according to one or more exemplary embodiments may display an assign indicator set by a workstation. Accordingly, a user may efficiently distinguish a plurality of X-ray detectors from one another and may efficiently select an X-ray detector that is to be used in X-ray imaging from among the X-ray detectors, by referring to the respective assign indicators of the X-ray detectors.

A workstation capable of setting assign indicator information of an X-ray detector and an X-ray detector capable of displaying an assign indicator, according to one or more exemplary embodiments, will now be described in detail.

Figure 5:
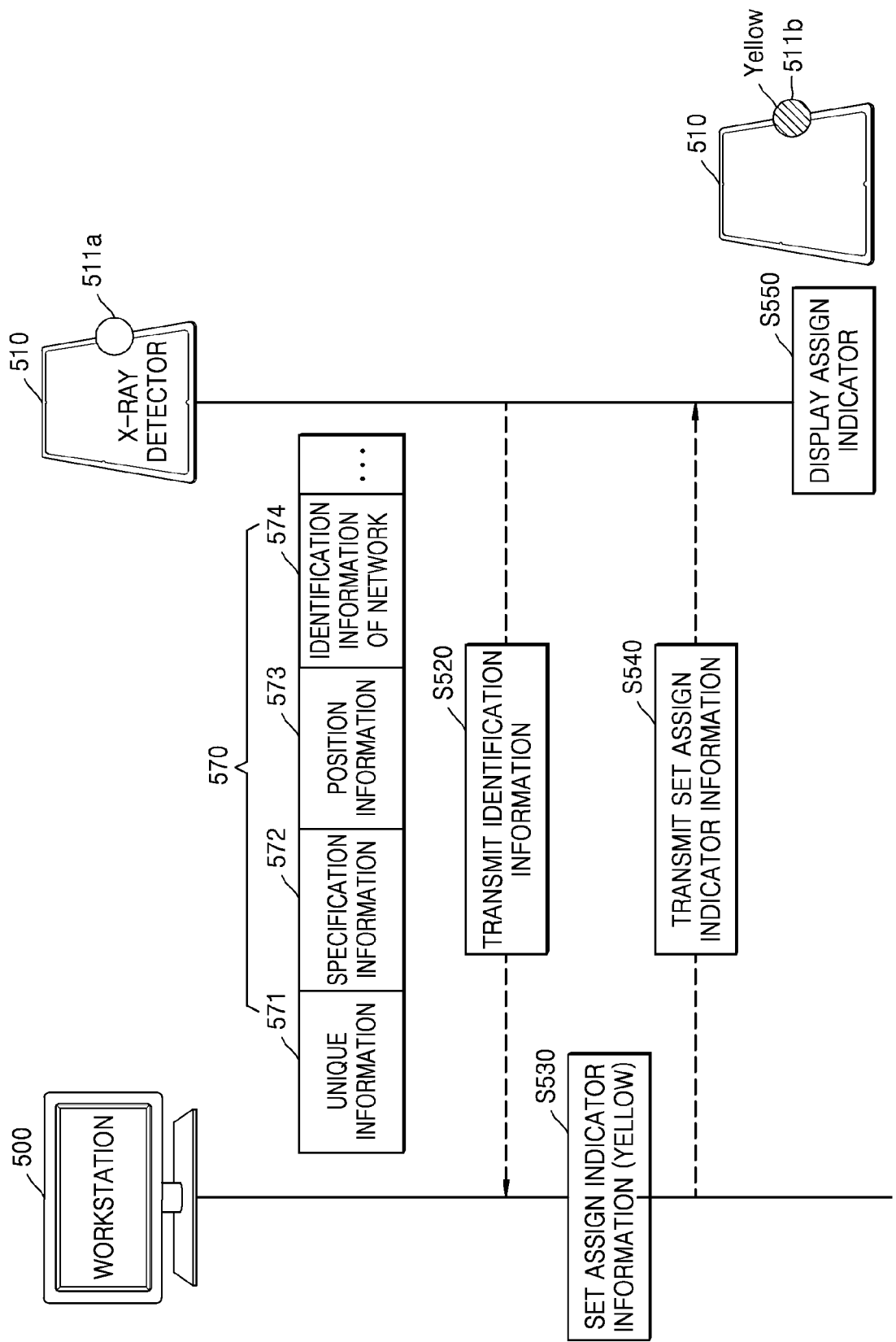
FIG. 5 is a diagram for explaining respective operations of a workstation and an X-ray detector according to an exemplary embodiment.

FIG. 5 is a block diagram for describing respective operations of a workstation 500 and an X-ray detector 510 according to an exemplary embodiment. The X-ray detector 510 includes an output unit 511a for displaying an assign indicator.

In operation S520, the X-ray detector 510 transmits identification information 570 of the X-ray detector 510 to the workstation 500. Throughout the specification, the identification information 570 of the X-ray detector 510 refers to predetermined information about the X-ray detector 510 that distinguishes the X-ray detector 510 from other X-ray detectors.

For example, the identification information 570 may include unique information 571 of the X-ray detector 510 that distinguishes the X-ray detector 510 from not only other types of X-ray detectors but also the same type of X-ray detectors as that of the X-ray detector 510. For example, the unique information 571 may include at least one selected from a serial number (SN) of the X-ray detector 510 and Internet Protocol (IP) address information thereof. In detail, the SN of the X-ray detector 510 is a unique identifier assigned during the manufacture of the X-ray detector 510. The IP address information of the X-ray detector 510 may include an IP address value that is to be used when the X-ray detector 510 and an access point (AP) communicate with each other.

The identification information 570 may also include specification information 572 of the X-ray detector 510 that distinguishes the X-ray detector 510 from other types of X-ray detectors. For example, the specification information 572 may include at least one selected from the size of the X-ray detector 510 and the type of a receptor with which the X-ray detector 510 is combinable. As described above, different sizes and shapes of X-ray detectors may be suitable for X-ray imaging according to parts of an object to be photographed. Accordingly, the size of the X-ray detector 510 may be a criterion on which a user selects an X-ray detector 510 suitable for imaging. In addition, when a user wants to combine the X-ray detector 510 to a predetermined receptor, the type of a receptor with which the X-ray detector 510 is combinable may be a criterion on which a user selects an X-ray detector 510 suitable for imaging.

For example, when a 17×17 inch X-ray detector 510 may be combined with the stand type receptor 280 of FIG. 2 by a user but a 14×14 inch X-ray detector 510 may be combined with the table type receptor 290 of FIG. 2, the specification information 572 of the X-ray detector 510 may be a criterion on which a user selects an X-ray detector suitable for imaging.

The specification information 572 of the X-ray detector 510 is not limited to the size of the X-ray detector 510 and the type of a receptor with which the X-ray detector 510 is combinable. For example, the specification information 572 of the X-ray detector 510 may further include information about a detection material of the X-ray detector 510, information about a geometrical structure of the X-ray detector 510, and information about a method in which the X-ray detector 510 measures a signal. In detail, the information about the detection material of the X-ray detector 510 includes a light detection type and a direct charge-detection type. The information about the geometrical structure of the X-ray detector 510 includes a one-dimensional (1D) array type and a two-dimensional (2D) area type. The information about the method in which the X-ray detector 510 measures a signal may include an integral detection type and a coefficient detection type.

In addition to the unique information 571 and the specification information 572, the identification information 570 of the X-ray detector 510 may further include position information 573 of the X-ray detector 510 and identification information 574 of a network to which the X-ray detector 510 has been connected. The position information 573 of the X-ray detector 510 and the identification information 574 of the network will be described in further detail later with reference to FIGS. 8, 9, 12, and 13.

In operation S530, the workstation 500 sets assign indicator information of the X-ray detector 510, based on the identification information 570 of the X-ray detector 510. Throughout the specification, an assign indicator refers to a visual indicator that is displayed by the output unit 511a of the X-ray detector 510, and may be a visual notification signal capable of helping a user to select an X-ray detector 510 which is to be used for imaging. Throughout the specification, assign indicator information refers to information used to control an assign indicator that the X-ray detector 510 displays. The workstation 500 sets the assign indicator information and transmits the assign indicator information to the X-ray detector 510. In detail, the assign indicator may include at least one selected from a character, a number, a symbol, a color, and an image. The assign indicator information may include information that indicates at least one selected from a character, a number, a symbol, a color, and an image.

In operation S540, the workstation 500 transmits the set assign indicator information to the X-ray detector 510.

In operation S550, the X-ray detector 510 displays an assign indicator based on the received assign indicator information. For example, when the workstation 500 sets, based on the specification information 572 of the X-ray detector 510, information indicating a yellow color as assign indicator information for a 17×17 inch X-ray detector 510 and sets information indicating a blue color as assign indicator information for a 14×14 inch X-ray detector 510, an output unit 511b of a 17×17 inch X-ray detector 510 may display an assign indicator corresponding to a yellow color.

A user may efficiently distinguish 14×14 inch X-ray detectors 510 from 17×17 inch X-ray detectors 510 by referring to assign indicators of a yellow or blue color displayed on the X-ray detectors 510. For example, when a 17×17 inch X-ray detector 510 is combinable with the stand type receptor 280, a user may easily select an X-ray detector 510 that displays the assign indicator of a yellow color and may combine the selected X-ray detector 510 with the stand type receptor 280.

Figure 6:
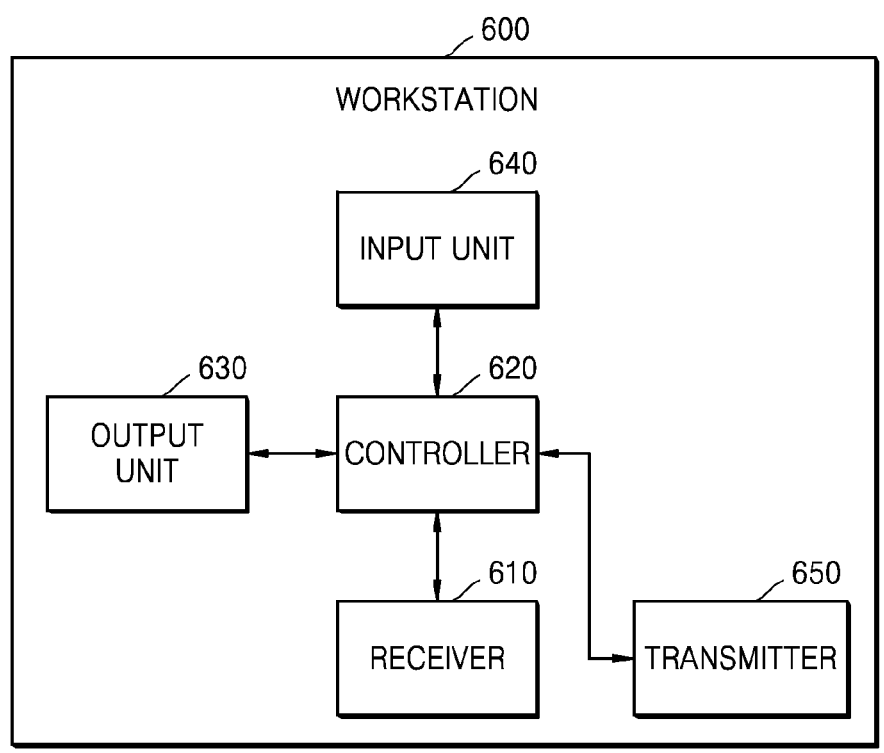
FIG. 6 is a schematic diagram of a workstation according to an exemplary embodiment.

FIG. 6 is a block diagram of a workstation 600 according to an exemplary embodiment. The workstation 600 includes a receiver 610, a controller 620, an output unit 630, and a transmitter 650, and may further include an input unit 640.

When the workstation 600 of FIG. 6 is included in the X-ray system 1000 of FIG. 1, the workstation 600 of FIG. 6 may correspond to the workstation 110 of FIG. 1. In detail, the controller 620, the output unit 630, and the input unit 640 of the workstation 600 of FIG. 6 may respectively correspond to the controller 113, the output unit 111, and the input unit 112 of the workstation 110 of FIG. 1. The receiver 610 and the transmitter 650 of the workstation 600 of FIG. 6 may communicate with the X-ray apparatus 100 by wires or wirelessly and may also communicate with an external apparatus via the network 160 of FIG. 1. Thus, a repeated description thereof will be omitted.

The receiver 610 of the workstation 600 may receive identification information 570 of an X-ray detector 510 from the X-ray detector 510. For example, when the workstation 600 of FIG. 6 is included in the X-ray system 1000 of FIG. 1, the receiver 610 may directly receive identification information 570 of an X-ray detector 510 corresponding to the detector 130 of FIG. 1 via communication with the X-ray detector 510. When an X-ray detector 510 is coupled to a receptor, the receiver 610 may indirectly receive identification information 570 of the X-ray detector 510 via communication with the receptor.

The controller 620 of the workstation 600 may set assign indicator information of the X-ray detector 510, based on the received identification information 570 of the X-ray detector 510.

As described above, the identification information 570 of the X-ray detector 510 may include at least one selected from unique information 571, specification information 572, position information 573, and identification information 574 of a network to which the X-ray detector 510 has been connected.

When the controller 620 sets the assign indicator information based on the unique information 571 included in the identification information 570 of the X-ray detector 510, an assign indicator displayed on an X-ray detector 510 may be distinguished from assign indicators displayed on all of other X-ray detectors 570.

When the controller 620 sets the assign indicator information based on the specification information 572 included in the identification information 570 of the X-ray detector, X-ray detectors 510 having identical specification information 572 may display identical assign indicators.

When the controller 620 sets the assign indicator information based on the position information 573 included in the identification information 570 of the X-ray detector, X-ray detectors 510 located at the same positions may display identical assign indicators. The position information 573 of an X-ray detector 510 may include at least one selected from information indicating that the X-ray detector 510 has been coupled to a stand type receptor (hereinafter, referred to as stand position information), information indicating that the X-ray detector 510 has been coupled to a table receptor (hereinafter, referred to as table position information), and information indicating that the X-ray detector 510 has not been coupled to any receptors (hereinafter, referred to as portable position information). However, the position information 573 of the X-ray detector 510 is not limited thereto, and the position information 573 of the X-ray detector 510 may include additional position information 573 obtained via a sensor in an X-ray imaging room or a sensor included in an X-ray system 1000. The assign indicator information set according to the position information 573 of the X-ray detector 510 will be described in further detail later with reference to FIGS. 8 and 9.

When the controller 620 sets the assign indicator information based on the identification information 574 of the network to which the X-ray detector 510 has been connected, which is included in the identification information 570 of the X-ray detector 510, X-ray detectors 510 connected to an identical network may display identical assign indicators. In detail, when each room of a plurality of X-ray imaging rooms use a different network, X-ray detectors 510 existing in an identical X-ray imaging room may display identical assign indicators, whereas X-ray detectors 510 existing in different X-ray imaging rooms may display different assign indicators. The assign indicator information set according to the identification information 574 of the network to which the X-ray detector 510 has been connected will be described in further detail later with reference to FIGS. 12 and 13.

The output unit 630 of the workstation 600 may display the assign indicator information of the X-ray detector 510 that has been set by the controller 620. In detail, the output unit 630 may display an X-ray detector icon representing the assign indicator information of the X-ray detector 510.

Accordingly, a user may efficiently distinguish the plurality of X-ray detectors 510 from one another and efficiently select an X-ray detector 510 that is to be used in imaging, by referring to not only an assign indicator displayed on an output unit 511a of the X-ray detector 510 but also the assign indicator information of the X-ray detector 510 displayed on the output unit 630 of the workstation 600.

The workstation 600 may further include the input unit 640 to receive a user input. The assign indicator information of the X-ray detector 510 may be arbitrarily set by the controller 620, and the set assign indicator information may be changed by a user. In detail, the input unit 640 may receive an input of re-setting the assign indicator information of the X-ray detector 510 set by the controller 620, and the controller 620 may re-set the assign indicator information of the X-ray detector 510 in response to the input.

Similarly, the controller 620 may select one of a plurality of identification information 570 of the X-ray detector 510 received by the receiver 610, as a criterion for setting the assign indicator information of the X-ray detector 510 (hereinafter, referred to as an assign indicator information setting criterion).

The assign indicator information setting criterion may be changed by a user. In detail, the input unit 640 may receive an input of changing the assign indicator information setting criterion selected by the controller 620, and the controller 620 may change the assign indicator information setting criterion in response to the input.

The input unit 640 may be a touch pad. In detail, the input unit 640 may include a touch pad (not shown) coupled with a display panel (not shown) included in the output unit 630. The output unit 630 displays a user interface (UI) image on the display panel. When a user inputs a command by touching a certain point on the UI image, the touch pad may sense the input operation and recognize the command input by the user.

In detail, when the input unit 640 is a touch pad and the user touches a certain point on the UI image, the input unit 640 senses the touched point. Then, the input unit 640 may transmit sensed information to the controller 620. Thereafter, the controller 620 may recognize a user's request or command corresponding to the sensed information and may perform the recognized user's request or command.

The transmitter 650 of the workstation 600 may transmit assign indicator information of the X-ray detector 510 to the X-ray detector 510. For example, when the workstation 600 of FIG. 6 is included in the X-ray system 1000 of FIG. 1, the transmitter 650 may directly transmit the assign indicator information of the X-ray detector 510 corresponding to the detector 130 of FIG. 1 via communication with the X-ray detector 510. When the X-ray detector 510 is combined with a receptor, the transmitter 650 may indirectly transmit the assign indicator information of the X-ray detector via 510 communication with the receptor.

The receiver 610 and the transmitter 650 of the workstation 600 of FIG. 6 may communicate with an external apparatus including the X-ray detector 510 via a wired or wireless network 160.

The workstation 600 may be implemented in the manipulation unit 140 of the X-ray apparatus 100 of FIG. 1.

In detail, in the X-ray apparatus 100 including the X-ray radiation unit 120 for radiating an X-ray onto an object and the manipulation unit 140 for manipulating the X-ray radiation unit 120, the manipulation unit 140 may include a receiver (corresponding to the receiver 610) for receiving the identification information 570 of the X-ray detector 510, a controller (corresponding to the controller 620) for setting the assign indicator information of the X-ray detector 510 based on the received identification information 570 of the X-ray detector 510, an output unit (corresponding to the output unit 630) for displaying the assign indicator information of the X-ray detector 510, and a transmitter (corresponding to the transmitter 650) for transmitting the assign indicator information of the X-ray detector 510 to the X-ray detector 510.

When the workstation 600 is implemented in the manipulation unit 140 of the X-ray apparatus 100 of FIG. 1, the X-ray detector 510 may display an assign indicator via communication with the manipulation unit 140 of the X-ray apparatus 100, without the workstation 110 provided outside the X-ray apparatus 100.

Figure 7:
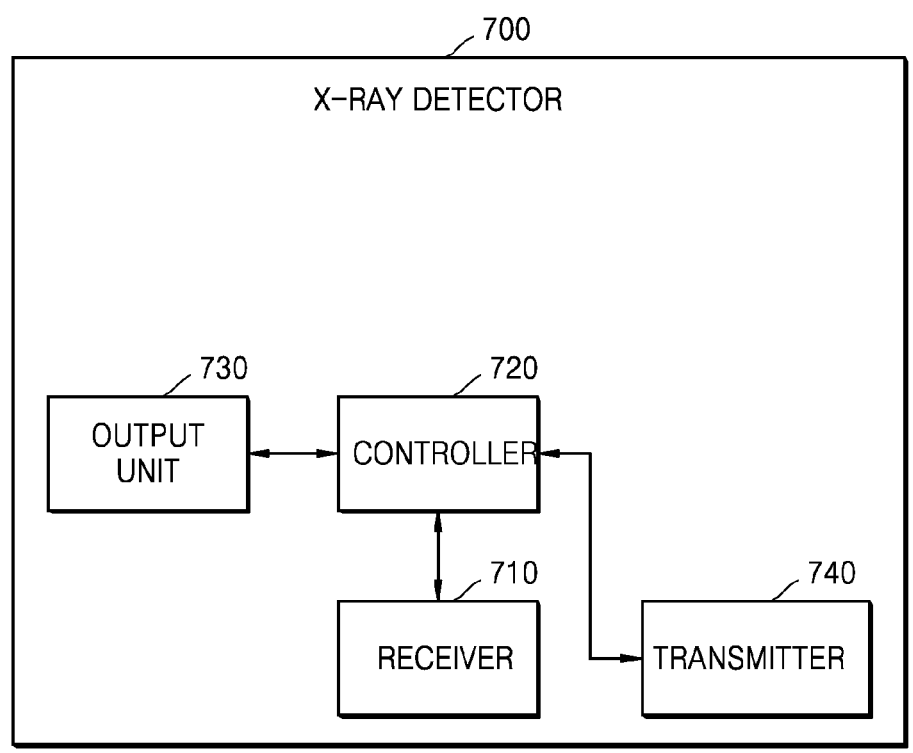
FIG. 7 is a block diagram of an X-ray detector according to an exemplary embodiment.

FIG. 7 is a block diagram of an X-ray detector 700 according to an exemplary embodiment.

The X-ray detector 700 may include a receiver 710, an output unit 730, and a transmitter 740. The X-ray detector 700 may further include a controller 720. When the X-ray detector 700 is included in the X-ray apparatus 100 of FIG. 1, the X-ray detector 700 may correspond to the detector 130 of FIG. 1. As described above, the X-ray detector 700 may be connected to or disconnected from the X-ray apparatus 100 of FIG. 1. Thus, a repeated description thereof will be omitted.

The transmitter 740 of the X-ray detector 700 may transmit the identification information of the X-ray detector 700 to a workstation. When the X-ray detector 700 is included in the X-ray system 1000 of FIG. 1, the transmitter 740 of the X-ray detector 700 may directly transmit the identification information of the X-ray detector 700 to the workstation 110 of FIG. 1. When the X-ray detector 700 is combined with a receptor of the X-ray apparatus 100, the transmitter 740 may indirectly transmit the identification information of the X-ray detector 700 to the workstation 110 via communication with the receptor.

After the transmitter 740 transmits the identification information, the receiver 710 of the X-ray detector 700 may receive the assign indicator information from the workstation 600. As described above, the assign indicator information may include information that indicates at least one selected from a character, a number, a symbol, a color, and an image.

When the X-ray detector 700 is included in the X-ray system 1000 of FIG. 1, the receiver 710 of the X-ray detector 700 may directly receive the assign indicator information from the workstation 110 of FIG. 1. When the X-ray detector 700 is combined with a receptor of the X-ray apparatus 100, the receiver 710 may indirectly receive assign indicator information from the workstation 110 via communication with the receptor.

The X-ray detector 700 may be a wired X-ray detector or a wireless X-ray detector. When the X-ray detector 700 is a wireless X-ray detector, the receiver 710 and the transmitter 740 may communicate with an external apparatus via a wireless network.

The output unit 730 of the X-ray detector 700 may display an assign indicator based on the assign indicator information received by the receiver 710 of the X-ray detector 700. For example, the output unit 730 of the X-ray detector 700 may include a liquid crystal display (LCD), a light-emitting diode (LED), or a light-emitting device to display the assign indicator.

The output unit 730 may include an optical waveguide positioned on at least one edge of the X-ray detector 700. The X-ray detector 700 may more efficiently display the assign indicator thereof via the optical waveguide. The optical waveguide will be described in further detail later with reference to FIGS. 19 and 20.

The controller 720 of the X-ray detector 700 may acquire state information of the X-ray detector 700. For example, the state information of the X-ray detector 700 may include at least one selected from residual battery capacity information of the X-ray detector 700, communication sensitivity information of the X-ray detector 700, and information about whether the X-ray detector 700 has been activated. The state information of the X-ray detector 700 will be described in further detail later with reference to FIGS. 14-18.

Figure 8:
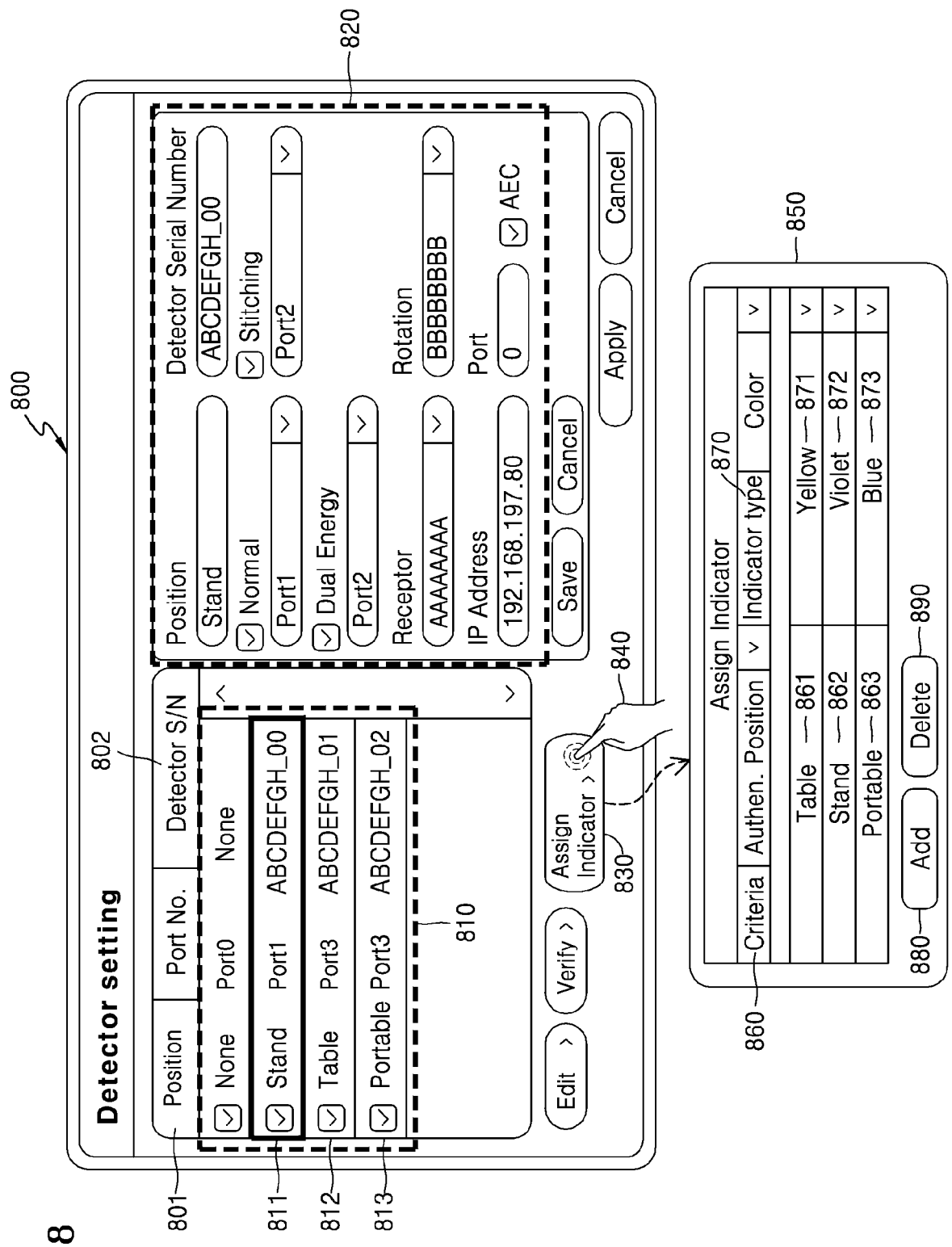
FIG. 8 illustrates an operation in which the workstation of FIG. 6 sets assign indicator information of an X-ray detector based on position information of the X-ray detector.

FIG. 8 illustrates an operation in which the workstation 600 of FIG. 6 sets the assign indicator information of an X-ray detector based on the position information of the X-ray detector. In detail, FIG. 8 illustrates UI images 800 and 850 displayed on the output unit 630 of the workstation 600.

Referring to FIGS. 6 and 8, the receiver 610 of the workstation 600 may receive the identification information of the X-ray detector that includes at least one selected from the unique information of the X-ray detector and the specification information of the X-ray detector and further includes the position information of the X-ray detector.

The controller 620 of the workstation 600 may authenticate the X-ray detector based on at least one selected from the unique information and the specification information of the X-ray detector which have been received by the receiver 610. For example, the workstation 600 may authenticate the X-ray detector based on a detector SN 802 of the X-ray detector.

Throughout the specification, authentication for an X-ray detector by a workstation means that a workstation previously registers an X-ray detector which is to be used in X-ray imaging. In addition, the workstation may allow an authenticated X-ray detector to communicate, or activate (or prepare for detection) the authenticated X-ray detector.

The output unit 630 of the workstation 600 may display a list 810 of X-ray detectors 811, 812, and 813 that have been authenticated by the workstation 600, via a UI image 800. The output unit 630 may simply display the identification information of the X-ray detector, such as the detector SN 802 and position information 801 of the X-ray detector, on the list 810 of the authenticated X-ray detectors.

The output unit 630 of the workstation 600 may also display more detailed identification information 820 of the X-ray detector 811 selected from among the list 810. The identification information 820 of the selected X-ray detector 811 may further include an IP address of the selected X-ray detector 811 and the type of a receptor with which the X-ray detector 811 is combinable, which are not shown on the list 810.

The controller 620 of the workstation 600 may set the assign indicator information of the authenticated X-ray detector based on the position information 801 of the X-ray detector. In other words, the controller 620 may set the position information 801 of the X-ray detector to be an assign indicator information setting criterion 860.

When the input unit 640 of the workstation 600 receives an input 840 of selecting an icon 830, the controller 620 may set respective assign indicator information of the X-ray detectors 811, 812, and 813. Alternatively, the controller 620 may set the respective assign indicator information of the X-ray detectors 811, 812, and 813 immediately without waiting until the input 840 for selecting an icon 830 is received.

In detail, the controller 620 may classify table position information 861, stand position information 862, and portable position information 863 of authenticated X-ray detectors and set identical assign indicator information for X-ray detectors having identical position information and different assign indicator information for X-ray detectors having different position information.

For example, the controller 620 may set assign indicator information 871 of a yellow color for an X-ray detector corresponding to the table position information 861, assign indicator information 872 of a violet color for an X-ray detector corresponding to the stand position information 862, and assign indicator information 873 of a blue color for an X-ray detector corresponding to the portable position information 863.

The position information of an X-ray detector may change as the position of the X-ray detector changes. For example, when an X-ray detector is a wireless X-ray detector, the X-ray detector may be combined with the stand type receptor 280 of FIG. 2 at a first point in time and may be separated from the stand type receptor 280 at a second point in time. Accordingly, the position information of the X-ray detector received by the receiver 610 of the workstation 600 at the first point in time may be stand position information, and the position information of the X-ray detector received by the receiver 610 of the workstation 600 at the second point in time may be portable position information.

Thus, the controller 620 needs to specify a point in time in order to set the assign indicator information of the X-ray detector based on the position information 801 of the X-ray detector. For example, the controller 620 of the workstation 600 may set the assign indicator information of the X-ray detector, based on position information of the X-ray detector at the point in time when the X-ray detector is authenticated.

In detail, the controller 620 of the workstation 600 may authenticate the X-ray detector based on at least one selected from the unique information and the specification information included in the identification information of the X-ray detector and may set the assign indicator information of the X-ray detector based on the position information included in the same identification information.

If the position information of the X-ray detector at the point in time when the X-ray detector is authenticated is stand position information, the X-ray detector may have a size and specifications that enable it to be combined with a stand type receptor. As another example, if the position information of the X-ray detector at the point in time when the X-ray detector is authenticated is table position information, the X-ray detector may have a size and specifications that enable it to be combined with a table type receptor. Accordingly, a user may easily ascertain the type of a receptor to which the X-ray detector is combinable, by referring to an assign indicator displayed on the X-ray detector.

The output unit 630 may display assign indicator information 870 of the X-ray detector that has been set by the controller 620. For example, the output unit 630 may display the assign indicator information 870 of the X-ray detector via the UI image 850. The output unit 630 may also display the assign indicator information setting criterion 860 via the UI image 850.

The input unit 640 may receive an input for re-setting the assign indicator information 871, the assign indicator information 872, and assign indicator information 873 that have been set by the controller 620. For example, the input unit 640 may receive an input for re-setting the assign indicator information of the X-ray detector corresponding to the table position information 861 to be a red color, via a UI image. The controller 620 may also re-set the assign indicator information of the X-ray detector in response to the input received by the input unit 640. The input unit 640 may receive an input for re-setting all of the assign indicator information 871, the assign indicator information 872, and the assign indicator information 873 to be an identical color.

The input unit 640 may also receive an input for re-setting the assign indicator information setting criterion 860 set by the controller 620. For example, the input unit 640 may receive an input for re-setting the assign indicator information setting criterion 860 to be a detector SN. Then, the controller 620 may re-set the assign indicator information setting criterion 860 of the X-ray detector, in response to the input received by the input unit 640.

The input unit 640 may also receive an input for adding assign indicator information of the X-ray detector. For example, when the input unit 640 receives an input for selecting an addition icon 880, the controller 620 may additionally set assign indicator information of a green color for an X-ray detector of which position information is not ascertained.

The input unit 640 may also receive an input of deleting assign indicator information of the X-ray detector. For example, the controller 620 may delete predetermined assign indicator information in response to an input of selecting a deletion icon 890 that the input unit 640 has received.

Figure 9:
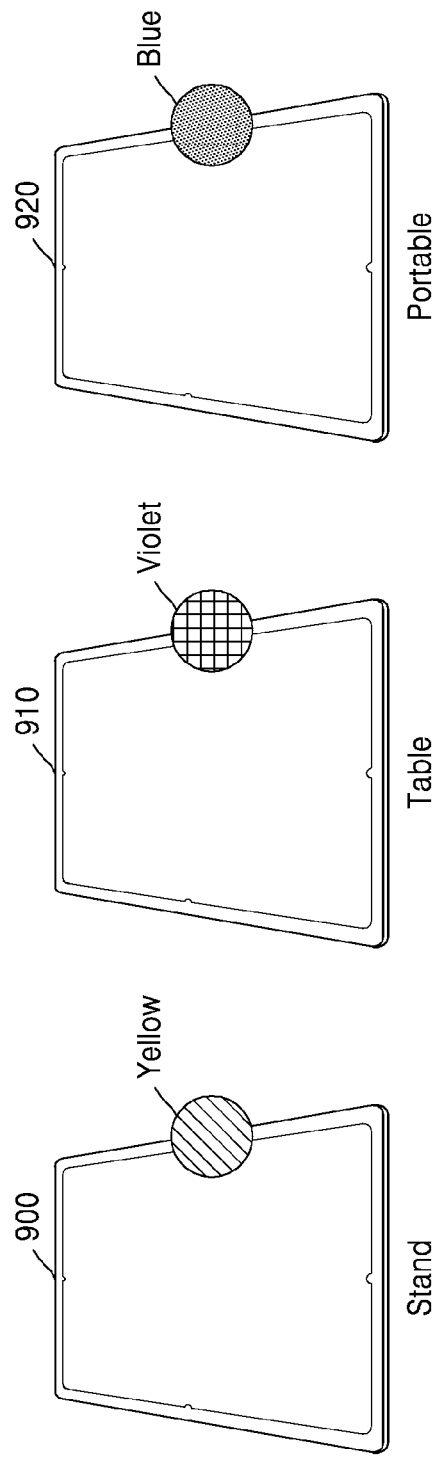
FIG. 9 illustrates respective operations of X-ray detectors according to the assign indicator information of FIG. 8.

FIG. 9 illustrates operations of X-ray detectors according to the assign indicator information 871, the assign indicator information 872, and the assign indicator information 873 of FIG. 8.

In detail, an X-ray detector 900 corresponding to stand position information may receive the assign indicator information 871, an X-ray detector 910 corresponding to table position information may receive the assign indicator information 872, and an X-ray detector 920 corresponding to portable position information may receive the assign indicator information 873.

An output unit of the X-ray detector 900 having the stand position information may display an assign indicator of a yellow color based on the assign indicator information 871 received by a receiver thereof, an output unit of the X-ray detector 910 having the table position information may display an assign indicator of a violet color based on the assign indicator information 872 received by a receiver thereof, and an output unit of the X-ray detector 920 having the portable position information may display an assign indicator of a blue color based on the assign indicator information 873 received by a receiver thereof.

The receivers of the X-ray detectors 900, 910, and 920 may also receive re-setting information used to reset the displayed assign indicators, respectively. For example, the receiver of the X-ray detector 900 having the stand position information may receive re-setting information used to reset the assign indicator to be a red color. Then, the output unit of the X-ray detector 900 having the stand position information may display an assign indicator of a red color.

As described above, a user may efficiently select an X-ray detector suitable for imaging environment by referring to the assign indicators displayed on the output units of the X-ray detectors 900, 910, and 920. For example, when an X-ray detector combinable with the table type receptor 290 is needed, a user may select the X-ray detector 910 that displays the assign indicator of a violet color.

Figure 10:
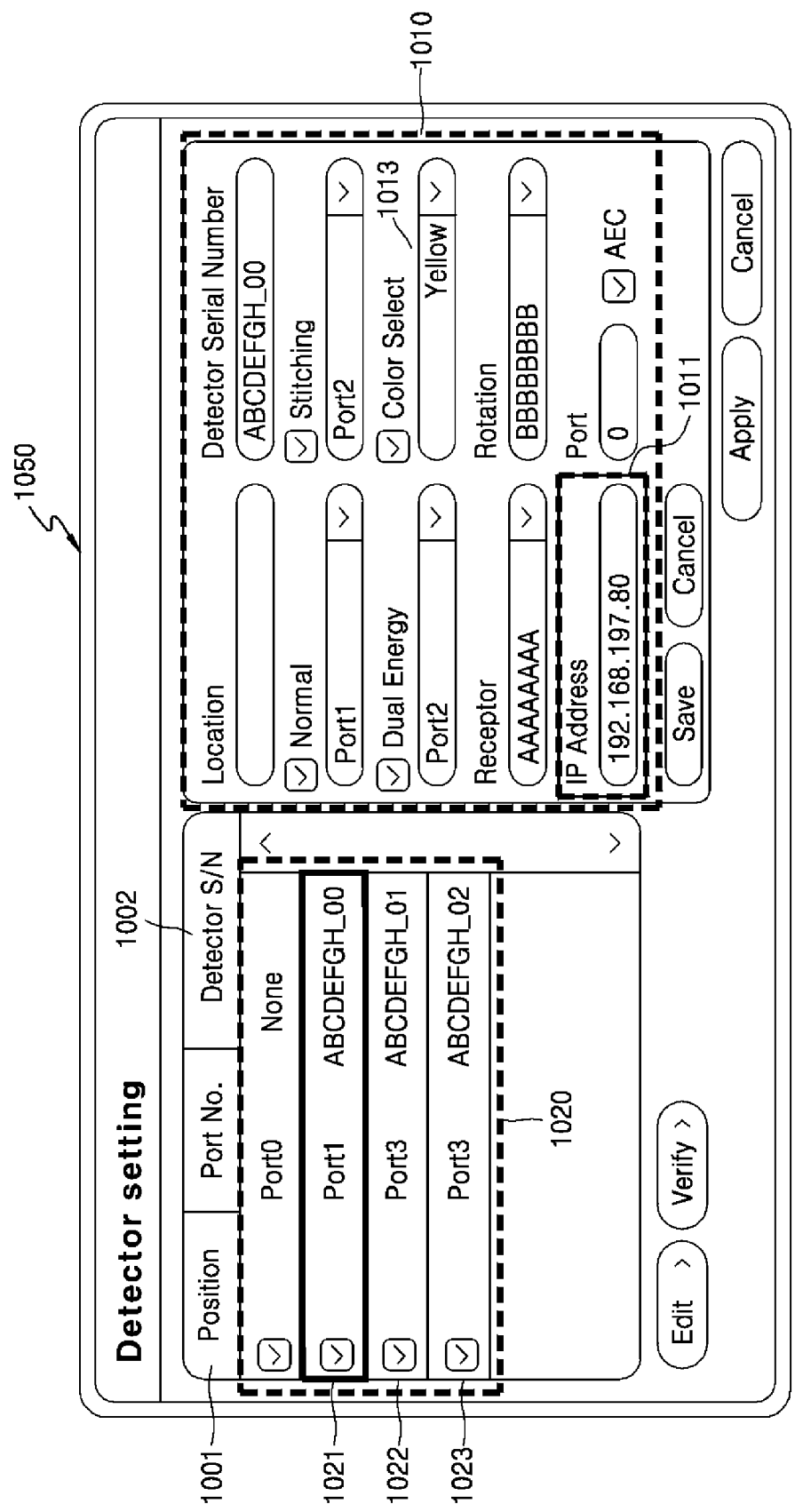
FIG. 10 illustrates an operation in which the workstation of FIG. 6 sets assign indicator information of an X-ray detector based on unique information of the X-ray detector.

FIG. 10 illustrates an operation in which the workstation 600 of FIG. 6 sets assign indicator information of an X-ray detector based on unique information of the X-ray detector. In detail, FIG. 10 illustrates a UI image 1050 displayed on the output unit 630 of the workstation 600.

The UI image 1050 of FIG. 10 may correspond to the UI image 800 of FIG. 8. Thus, a repeated description thereof will be omitted.

Referring to FIGS. 6 and 10, the receiver 610 of the workstation 600 may receive identification information of the X-ray detector that includes at least one selected from the unique information of the X-ray detector and specification information of the X-ray detector. In contrast with FIG. 8, the identification information of the X-ray detector may not include position information of the X-ray detector.

The controller 620 of the workstation 600 may authenticate the X-ray detector based on at least one selected from the unique information and the specification information of the X-ray detector which have been received by the receiver 610. For example, the workstation 600 may authenticate the X-ray detector based on a detector SN 1002 of the X-ray detector.

The output unit 630 of the workstation 600 may display a list 1020 of X-ray detectors 1021, 1022, and 1023 that have been authenticated by the workstation 600, via the UI image 1050. The output unit 630 of the workstation 600 may display detailed identification information 1010 of the X-ray detector 1021 selected from the list 1020 of authenticated X-ray detectors.

The controller 620 of the workstation 600 may set assign indicator information of the authenticated X-ray detector 1021 based on an IP address 1011 of the X-ray detector 1021. In other words, the controller 620 may set the IP address 1011 of the X-ray detector 1021 to be an assign indicator information setting criterion.

In general, an X-ray detector has a unique IP address. Accordingly, the controller 620 may classify respective IP addresses of the authenticated X-ray detectors 1021, 1022, and 1023 and set unique assign indicator information for each of the authenticated X-ray detectors 1021, 1022, and 1023. However, when the authenticated X-ray detectors 1021, 1022, and 1023 have identical IP addresses, the controller 620 may set identical assign indicator information for each of the authenticated X-ray detectors 1021, 1022, and 1023.

For example, as described in further detail later with reference to FIG. 11, the controller 620 may set assign indicator information 1013 of a yellow color for the X-ray detector 1021 having the IP address 1011 of 191.168.197.80, set assign indicator information (not shown) of a violet color for the X-ray detector 1022 having an IP address (not shown) of 191.168.197.81, and set assign indicator information (not shown) of a blue color for the X-ray detector 1023 having an IP address (not shown) of 191.168.197.82.

The input unit 640 may receive an input for re-setting the assign indicator information 1013 that has been set by the controller 620. For example, the input unit 640 may receive an input for re-setting the assign indicator information 1013 of the X-ray detector 1021 corresponding to the IP address 1011 of 191.168.197.80 to be a red color, via a UI image (not shown). The controller 620 may also re-set the assign indicator information of the X-ray detector in response to the input received by the input unit 640.

Figure 11:
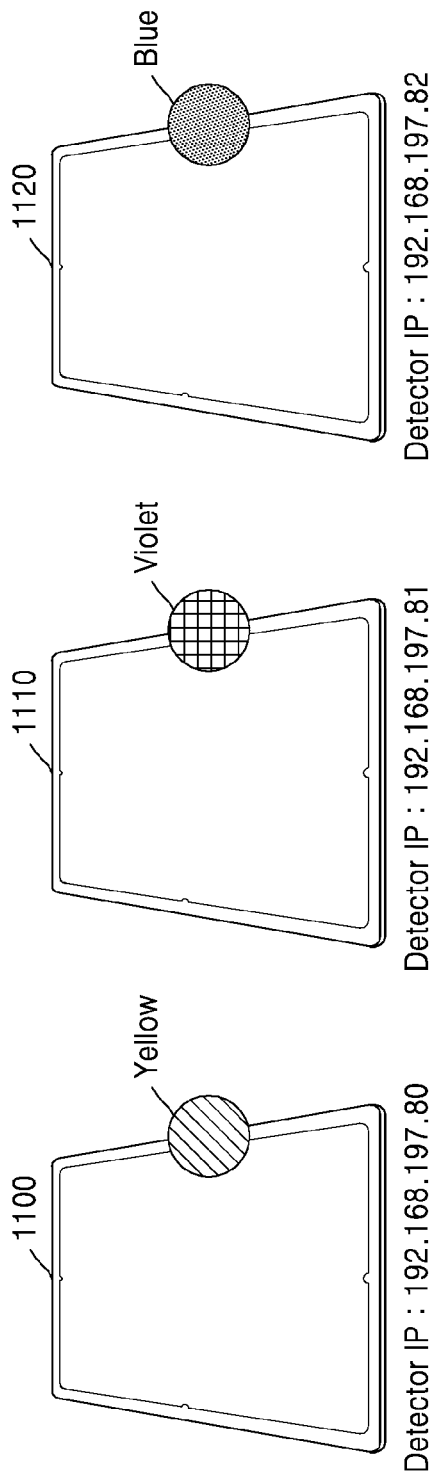
FIG. 11 illustrates respective operations of X-ray detectors according to the assign indicator information of FIG. 10.

FIG. 11 illustrates respective operations of X-ray detectors 1100, 1110, and 1120 according to the assign indicator information of FIG. 10.

In detail, receivers of the X-ray detectors 1100, 1110, and 1120 respectively receive the assign indicator information of FIG. 10 set by the workstation 600.

Based on the assign indicator information received by the receivers, an output unit of X-ray detector 1100 having the IP address of 191.168.197.80 may display an assign indicator of a yellow color, an output unit of X-ray detector 1110 having the IP address of 191.168.197.81 may display an assign indicator of a violet color, and an output unit of X-ray detector 1120 having the IP address of 191.168.197.82 may display an assign indicator of a blue color.

The receivers of the X-ray detectors 1100, 1110, and 1120 may also receive re-setting information used to reset the displayed assign indicators, respectively. For example, the receiver of the X-ray detector 1100 having the IP address of 191.168.197.80 may receive re-setting information used to reset the assign indicator to be a red color. Then, the output unit of the X-ray detector 1100 may display an assign indicator of a red color.

As described above, a user may efficiently select an X-ray detector suitable for imaging environment by referring to the assign indicators displayed on the X-ray detectors 1100, 1110, and 1120. For example, when X-ray detectors display respective unique assign indicators according to IP addresses, a user may efficiently select a frequently-used X-ray detector according to imaging environments by referring to the respective unique assign indicators of the X-ray detectors.

Figure 12:
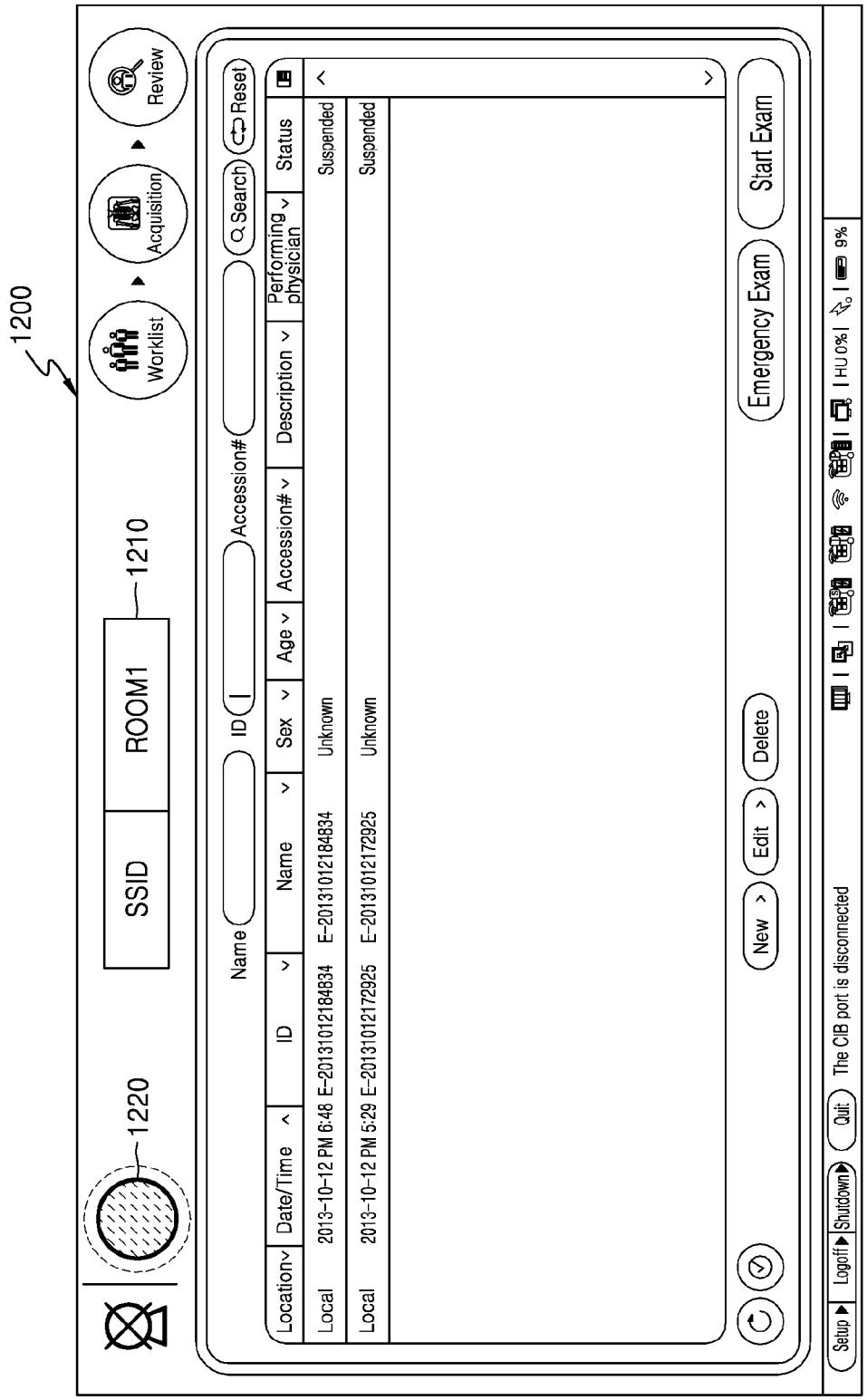
FIG. 12 illustrates an operation in which the workstation of FIG. 6 sets assign indicator information of an X-ray detector based on identification information of a network to which the X-ray detector has been connected.

FIG. 12 illustrates an operation in which the workstation 600 of FIG. 6 sets assign indicator information of an X-ray detector based on identification information of a network to which the X-ray detector has been connected. In detail, FIG. 12 illustrates a UI image 1200 displayed on the output unit 630 of the workstation 600. In detail, the output unit 630 may display identification information 1210 of the network to which the X-ray detector has been connected, and assign indicator information 1220 of the X-ray detector, via the UI image 1200.

When an X-ray detector is separable from an X-ray apparatus, a user may use the X-ray detector in different X-ray apparatuses existing in a plurality of X-ray imaging rooms. Thus, the user needs to check an X-ray imaging room including an initially-authenticated X-ray detector in order to efficiently manage X-ray detectors.

For example, when different X-ray imaging rooms use different networks, the identification information of a network to which an X-ray detector has been connected when it is initially authenticated may be an assign indicator information setting criterion.

Referring to FIGS. 6 and 12, the receiver 610 of the workstation 600 may receive the identification information of the X-ray detector that includes at least one selected from the unique information of the X-ray detector and the specification information of the X-ray detector and further includes the identification information of the network to which the X-ray detector has been connected. In contrast with FIG. 8, the identification information of the X-ray detector may not include position information of the X-ray detector.

The controller 620 of the workstation 600 may authenticate the X-ray detector based on at least one selected from the unique information and the specification information of the X-ray detector which have been received by the receiver 610. For example, the workstation 600 may authenticate the X-ray detector based on a detector SN of the X-ray detector.

The controller 620 of the workstation 600 may set the assign indicator information 1220 of the authenticated X-ray detector based on the identification information 1210 of the network to which the X-ray detector has been connected. In other words, the controller 620 may set the identification information 1210 of the network to which the X-ray detector has been connected to be an assign indicator information setting criterion.

For example, the identification information of the network to which the X-ray detector has been connected may include a service set identifier (SSID). An SSID is a unique identifier of a 32 byte length that is added to the header of each packet that is transmitted via a wireless LAN included in an X-ray imaging room, and may be used as a password when wireless devices such as wireless X-ray detectors are connected to a basic service set (BSS). Since an SSID distinguishes a wireless LAN (e.g., the wireless LAN of a first X-ray imaging room) from another wireless LAN (e.g., the wireless LAN of a second X-ray imaging room), all APs or wireless devices that are trying to access a predetermined wireless LAN need to use an identical SSID. If a wireless device does not know the unique SSID of a BSS, the wireless device cannot access the BSS. Accordingly, such an SSID may be used as the identification information of an imaging space.

For example, the controller 620 may set the assign indicator information 1220, which is a red color, for the X-ray detector corresponding to the identification information 1210 of the network that indicates the SSID of the first imaging room.

The input unit 640 may receive an input for re-setting the assign indicator information 1220 of the X-ray detector that has been set by the controller 620. For example, the input unit 640 may receive an input for re-setting the assign indicator information 1220 of the X-ray detector to be a blue color, via a UI image (not shown). The controller 620 may also re-set the assign indicator information 1220 of the X-ray detector in response to the input received by the input unit 640.

FIG. 13 illustrates respective operations of X-ray detectors 1301, 1302, and 1303 according to the assign indicator information of FIG. 12.

In detail, receivers (not shown) of the X-ray detectors 1301, 1302, and 1303 respectively receive the assign indicator information of FIG. 12 set by the workstation 600. Based on the assign indicator information received by the receivers, output units 1311, 1312, and 1313 of the X-ray detectors 1301, 1302, and 1303 having identification information of a network indicating the SSID of a first imaging room may display an assign indicator of a red color.

The receivers of the X-ray detectors 1301, 1302, and 1303 may also receive re-setting information used to reset the displayed assign indicators, respectively.

As described above, a user may check an X-ray imaging room including an initially-authenticated X-ray detector and efficiently manage X-ray detectors, by referring to the assign indicators of the X-ray detectors 1301, 1302, and 1303.

The X-ray detectors 1301, 1302, and 1303 may include a plurality of output units 1311-1313, a plurality of output units 1321-1323, and a plurality of output units 1331-1333, respectively, in order for each of the X-ray detectors 1301, 1302, and 1303 to display a plurality of assign indicators. For example, the output units 1311, 1312, and 1313 of the X-ray detectors 1301, 1302, and 1303 may display assign indicators set based on identification information of networks, and the other output units 1321-1323 and 1331-1333 thereof may display assign indicators set based on another assign indicator information setting criterion.

For example, the output unit 1321 of the X-ray detector 1301 having stand position information during authentication may display an assign indicator of a yellow color, like the output unit of the X-ray detector 900 of FIG. 9. The output unit 1322 of the X-ray detector 1302 having table position information during authentication may display an assign indicator of a violet color, like the output unit of the X-ray detector 910 of FIG. 9. The output unit 1323 of the X-ray detector 1303 having portable position information during authentication may display an assign indicator of a blue color, like the output unit of the X-ray detector 920 of FIG. 9.

As another example, the output units 1331, 1332, and 1333 of the X-ray detectors 1301, 1302, and 1303 may display assign indicators set based on respective specification information thereof, respectively.

FIG. 14 is a block diagram for describing respective operations of a workstation 1400 and an X-ray detector 1410 according to another exemplary embodiment.

In operation S1420, a controller of the X-ray detector 1410 may acquire state information 1480 of the X-ray detector 1410.

Throughout the specification, state information of an X-ray detector refers to information about the conditions under which the X-ray detector detects an X-ray. For example, the state information of the X-ray detector may include at least one selected from residual battery capacity information of the X-ray detector, communication sensitivity information of the X-ray detector, and information about whether the X-ray detector has been activated.

In operation S1450, an output unit 1411b of the X-ray detector 1410 may display the state information 1480 and an assign indicator of the X-ray detector 1410. For example, the output unit 1411b of the X-ray detector 1410 may alternately display the state information 1480 and the assign indicator of the X-ray detector 1410. Alternatively, the output unit 1411*b* of the X-ray detector 1410 may simultaneously display the state information 1480 and the assign indicator of the X-ray detector 1410. For example, the X-ray detector 1410 may display residual battery capacity information and communication sensitivity information on an assign indicator of a yellow color. A method by which the output unit 1411*b* of the X-ray detector 1410 displays the state information 1480 and the assign indicator of the X-ray detector 1410 will be described in further detail later with reference to FIG. 15.

A user may check the state information of the X-ray detector 1410 displayed on the output unit 1411*b* of the X-ray detector 1410 and may efficiently manage X-ray detectors.

In operation S1430, a receiver of the workstation 1400 may receive the state information 1480 of the X-ray detector 1410. In operation S1440, an output unit of the workstation 1400 may display an X-ray detector icon 1401 representing the state information 1480 of the X-ray detector 1410 and assign indicator information of the X-ray detector 1410.

In detail, a transmitter of the X-ray detector 1410 may transmit a data packet including the state information 1480 of the X-ray detector 1410 and identification information 1490 of the X-ray detector 1410 to the workstation 1400. The identification information 1490 of the X-ray detector 1410 may include at least one selected from unique information 1491 and specification information 1492 of the X-ray detector 1410.

The receiver of the workstation 1400 may receive the data packet including the state information 1480 of the X-ray detector 1410 and identification information 1490 of the X-ray detector 1410, and a controller of the workstation 1400 may identify the X-ray detector 1410 that has transmitted the data packet, based on the identification information 1490 of the X-ray detector 1410. The output unit of the workstation 1400 may display the X-ray detector icon 1401 representing the state information 1480 of the X-ray detector 1410 specified by the controller thereof and the assign indicator information of the X-ray detector 1410.

Alternatively, the output unit of the workstation 1400 may display an X-ray detector icon 1401 representing the identification information 1490 of the X-ray detector 1410 specified by the controller thereof and the assign indicator information of the X-ray detector 1410. The X-ray detector icon 1401 will be described in further detail later with reference to FIG. 16.

A user may check the state information 1480 of the X-ray detector 1410 via the X-ray detector icon 1401 and may efficiently manage X-ray detectors. In addition, the user may easily activate the X-ray detector 1410 or may connect or block communication with the X-ray detector 1410, via the X-ray detector icon 1401.

As described above, a user may efficiently select an X-ray detector suitable for imaging environment and also may efficiently manage the states of X-ray detectors, by using the output unit 1411*b* of the X-ray detector 1410 and the output unit of the workstation 1400.

Figure 15A:
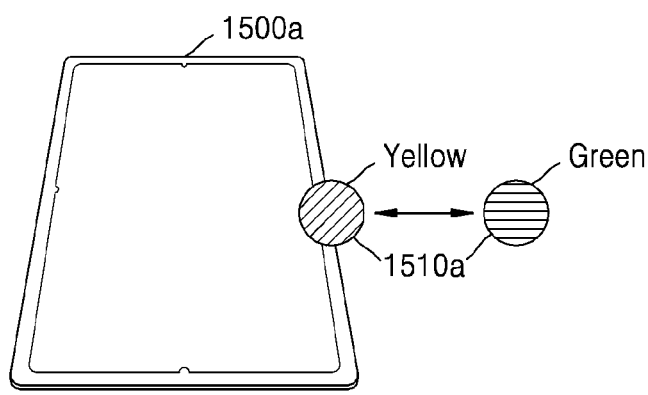
FIGS. 15A and 15B illustrate X-ray detectors on each of which an assign indicator and state information are displayed.
Figure 15B:
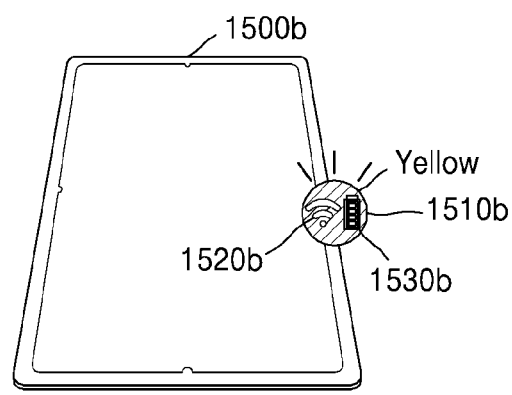

FIGS. 15A and 15B illustrate X-ray detectors 1500*a* and 1500*b* on which an assign indicator and state information are displayed.

An output unit 1510*a* of the X-ray detector 1500*a* may alternately display state information and an assign indicator of the X-ray detector 1500*a*.

In detail, a controller of the X-ray detector 1500*a* may set information that is to be output by the output unit 1510*a* of the X-ray detector 1500*a*, based on the state information of the X-ray detector 1500*a*. For example, the controller of the X-ray detector 1500*a* may control the output unit 1510*a* thereof to display a green color when residual battery capacity information is 50 to 100%, to display an orange color when the residual battery capacity information is 10 to 49%, and to display a red color when the residual battery capacity information is 0 to 9%.

The controller of the X-ray detector 1500*a* may control the output unit 1510*a* thereof to alternately display the assign indicator and the state information. For example, the output unit 1510*a* of the X-ray detector 1500*a*, for which the residual battery capacity is 100% and an assign indicator of a yellow color is set, may alternately display a yellow color as the assign indicator and a green color as the residual battery capacity information.

An output unit 1510*b* of the X-ray detector 1500*b* may simultaneously display state information and an assign indicator of the X-ray detector 1500*b*. For example, the X-ray detector 1500*b* may display a residual battery capacity information icon 1510*b* and a communication sensitivity information icon 1530*b* on an assign indicator of a yellow color.

The output unit 1520*b* of the X-ray detector 1500*b* may flicker the assign indicator based on the state information of the X-ray detector 1500*b*. For example, when the X-ray detector 1500*b* is activated, the residual battery capacity information of the X-ray detector 1500*b* is 9% or less, or the communication sensitivity of the X-ray detector 1500*b* is weak, the output unit 1510*b* of the X-ray detector 1500*b* may flicker the assign indicator.

Figure 16:
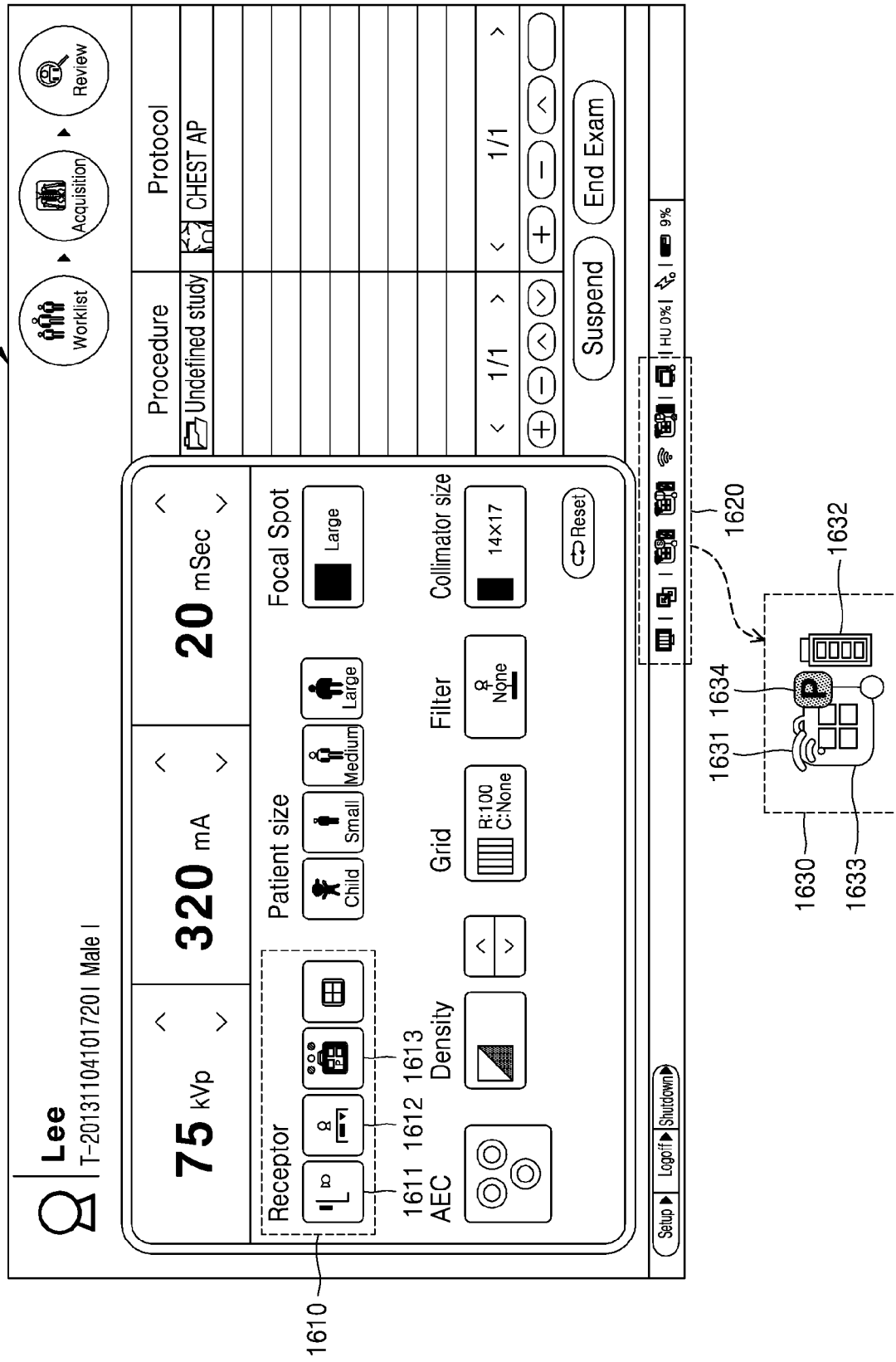
FIG. 16 illustrates an operation in which the workstation of FIG. 6 displays an X-ray detector icon, according to an exemplary embodiment.

FIG. 16 illustrates an operation in which the workstation 600 of FIG. 6 displays receptor information 1610 and an X-ray detector icon 1630, according to an exemplary embodiment.

For example, the receptor information may display an icon 1611 for activating an X-ray detector corresponding to stand position information, an icon 1612 for activating an X-ray detector corresponding table position information, and an icon 1630 for activating an X-ray detector corresponding to portable position information.

For example, the output unit 630 of the workstation 600 may display the X-ray detector icon 1630 on a UI image 1600 for setting X-ray imaging conditions. In detail, the output unit 630 of the workstation 600 may display the X-ray detector icon 1630 on a task bar 1620 of the UI image 1600.

The X-ray detector icon 1630 may represent identification information of an X-ray detector and assign indicator information thereof. In detail, the X-ray detector icon 1630 may include a sub-icon that represents the identification information of the X-ray detector and the assign indicator information thereof.

For example, when an assign indicator of the X-ray detector is a yellow color and the X-ray detector corresponds to portable position information, the X-ray detector icon 1630 may include a sub-icon 1634 of a character P with a yellow background. The sub-icon 1634 representing the position information of the X-ray detector may indicate a current position of the X-ray detector regardless of position information of the X-ray detector at the point in time when the X-ray detector is authenticated.

Based on specification information of the X-ray detector, the X-ray detector icon 1630 may include a sub-icon 1633 representing that the X-ray detector is a wireless X-ray detector.

The X-ray detector icon 1630 may further include a sub-icon that represents state information of the X-ray detector. For example, the X-ray detector icon 1630 may include a sub-icon 1632 representing residual battery capacity information of the X-ray detector and a sub-icon 1631 representing communication sensitivity information of the X-ray detector.

As described above, a user may easily activate the X-ray detector or may connect or block communication with the X-ray detector, via the X-ray detector icon 1630.

In addition, the user may ascertain all of the assign indicator of the X-ray detector and the identification information or state information of the X-ray detector via the X-ray detector icon 1630, thereby efficiently manage and control X-ray detectors.

FIGS. 17A-18B illustrate an operation in which the workstation 600 of FIG. 6 activates an X-ray detector, according to one or more exemplary embodiments.

Figure 17A:
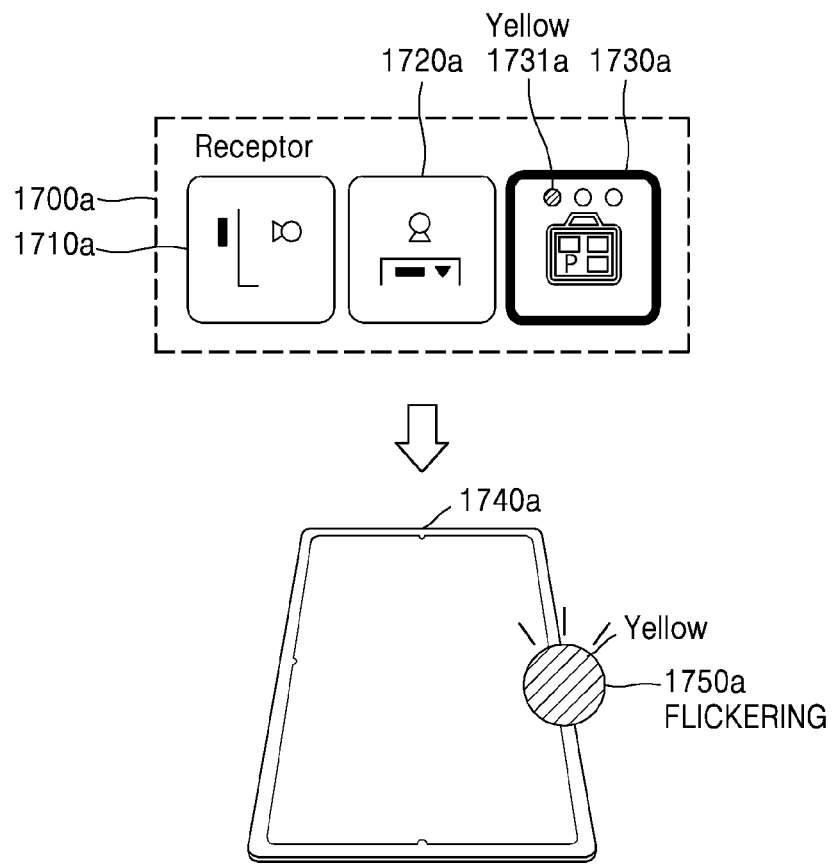

FIG. 17A illustrates an operation in which the workstation 600 activates an X-ray detector 1740a displaying an assign indicator of a yellow color and corresponding to current portable position information.

In detail, since the X-ray detector 1740a has been combined with the stand type receptor 280 when being authenticated by the workstation 600, the X-ray detector 1740a displays the assign indicator of a yellow color, like the X-ray detector 900 of FIG. 9. However, since the X-ray detector 1740a is not currently combined with any receptor, current position information of the X-ray detector 1740a corresponds to portable position information.

Icons included in receptor information 1700a may correspond to those included in receptor information 1610 of the UI screen 1600 of FIG. 16. In detail, an icon 1710a for activating an X-ray detector corresponding to stand position information corresponds to the icon 1611 of FIG. 16, an icon 1720a for activating an X-ray detector corresponding to table position information corresponds to the icon 1612 of FIG. 16, and an icon 1730a for activating an X-ray detector corresponding to portable position information corresponds to the icon 1613 of FIG. 16. For convenience of explanation, illustration of a portion of the UI screen 1600 except for the receptor information 1700a is omitted.

An output unit 1750a of the X-ray detector 1740a may flicker the assign indicator when the X-ray detector 1740a is activated.

The output unit 630 of the workstation 600 may display an X-ray detector icon 1760a based on identification information of the X-ray detector 1740a, assign indicator thereof, and state information thereof. In detail, the X-ray detector icon 1760a may represent that the X-ray detector 1740a is a wireless X-ray detector, corresponds to current portable position information, displays the assign indicator of a yellow color, and has high communication sensitivity and a residual battery capacity of 100%. When the X-ray detector 1740a is activated, a sub-icon 1770a representing the assign indicator may flicker.

FIG. 17B illustrates an operation in which the workstation 600 activates an X-ray detector 1740b displaying an assign indicator of a violet color and corresponding to current portable position information.

In detail, since the X-ray detector 1740b has been combined with the table type receptor 290 when being authenticated by the workstation 600, the X-ray detector 1740b displays the assign indicator of a violet color, like the X-ray detector 910 of FIG. 9. However, since the X-ray detector 1740b is not currently combined with any receptors, current position information of the X-ray detector 1740b corresponds to portable position information.

An output unit 1750b of the X-ray detector 1740b may flicker the assign indicator when the X-ray detector 1740b is activated.

The output unit 630 of the workstation 600 may display an X-ray detector icon 1760b based on identification information of the X-ray detector 1740b, assign indicator thereof, and state information thereof. In detail, the X-ray detector icon 1760b may represent that the X-ray detector 1740b is a wireless X-ray detector, corresponds to current portable position information, displays the assign indicator of a violet color, and has high communication sensitivity and a residual battery capacity of 100%. When the X-ray detector 1740b is activated, a sub-icon 1770b representing the assign indicator may flicker.

FIG. 17C illustrates an operation in which the workstation 600 activates an X-ray detector 1740c displaying an assign indicator of a blue color and corresponding to current portable position information.

In detail, since the X-ray detector 1740c has not been combined with any receptors when being authenticated by the workstation 600 and thus corresponds to portable position information, the X-ray detector 1740c displays the assign indicator of a blue color, like the X-ray detector 920 of FIG. 9. Furthermore, since the X-ray detector 1740c is not currently combined with any receptors, current position information of the X-ray detector 1740c corresponds to portable position information.

An output unit 1750c of the X-ray detector 1740c may flicker the assign indicator when the X-ray detector 1740c is activated.

The output unit 630 of the workstation 600 may display an X-ray detector icon 1760c based on identification information of the X-ray detector 1740c, assign indicator thereof, and state information thereof. In detail, the X-ray detector icon 1760c may represent that the X-ray detector 1740c is a wireless X-ray detector, corresponds to current portable position information, displays the assign indicator of a blue color, and has high communication sensitivity and a residual battery capacity of 100%. When the X-ray detector 1740c is activated, a sub-icon 1770c representing the assign indicator may flicker.

Figure 18A:
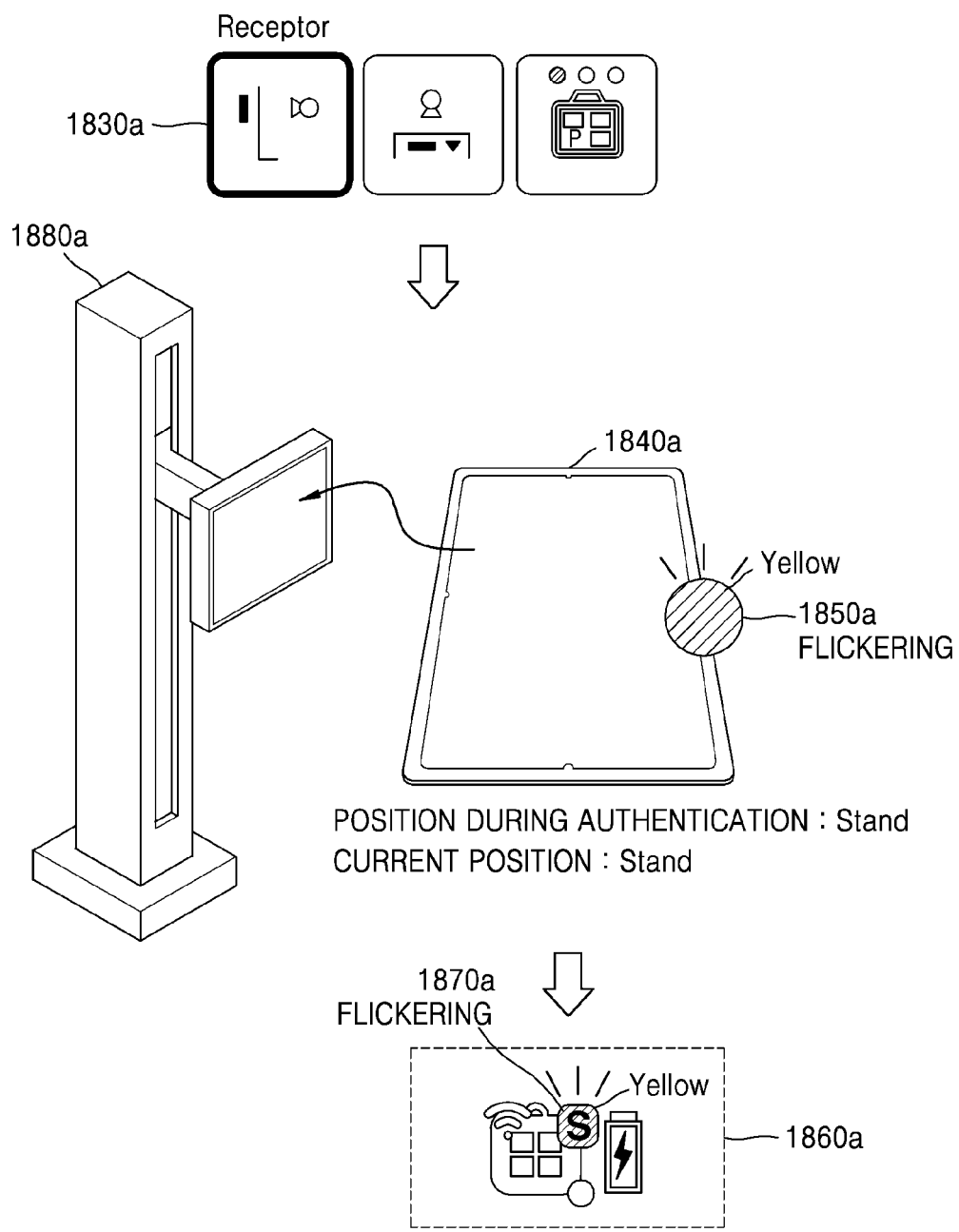

FIG. 18A illustrates an operation in which the workstation 600 activates an X-ray detector 1840a that displays an assign indicator of a yellow color and has been currently combined with a stand type receptor 1880a.

In detail, since the X-ray detector 1840a has been combined with the stand type receptor 1880a when being authenticated by the workstation 600, the X-ray detector 1840a displays the assign indicator of a yellow color, like the X-ray detector 900 of FIG. 9. Furthermore, since the X-ray detector 1840a is currently combined with the stand type receptor 1880a, current position information of the X-ray detector 1840a corresponds to stand position information.

An output unit 1850a of the X-ray detector 1840a may flicker the assign indicator when the X-ray detector 1840a is activated.

The output unit 630 of the workstation 600 may display an X-ray detector icon 1860a based on identification information of the X-ray detector 1840a, assign indicator thereof, and state information thereof. In detail, the X-ray detector icon 1860a may represent that the X-ray detector 1840a is a wireless X-ray detector, corresponds to current stand position information, displays the assign indicator of a yellow color, and has high communication sensitivity and a residual battery capacity of 9% or less. When the X-ray detector 1840*a* is activated, a sub-icon 1870*a* representing the assign indicator may flicker.

Figure 18B:
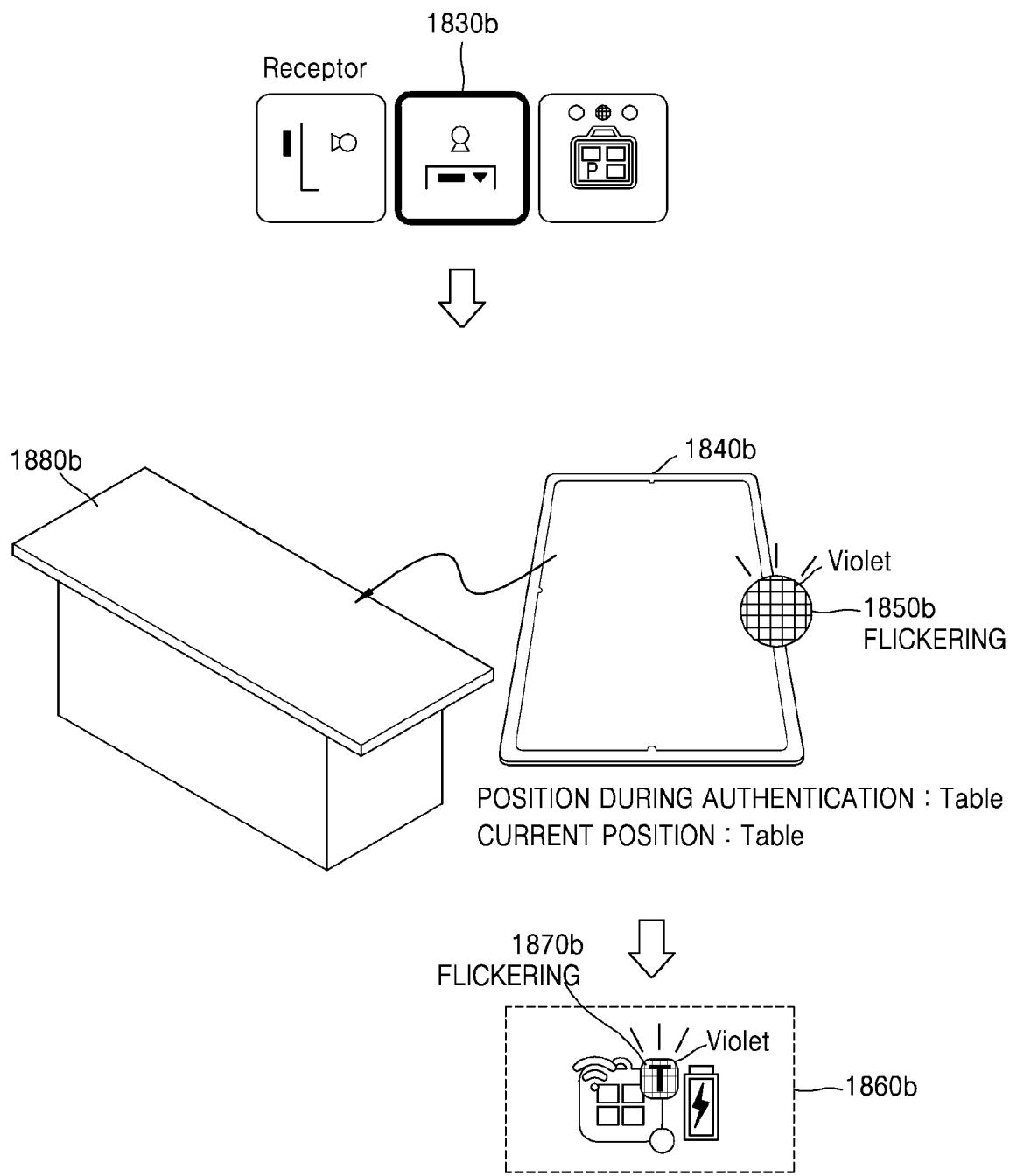

FIG. 18B illustrates an operation in which the workstation 600 activates an X-ray detector 1840*b* that displays an assign indicator of a violet color and has been currently combined with a table type receptor 1880*b*.

In detail, since the X-ray detector 1840*b* has been combined with the table type receptor 1880*b* when being authenticated by the workstation 600, the X-ray detector 1840*b* displays the assign indicator of a violet color, like the X-ray detector 910 of FIG. 9. Furthermore, since the X-ray detector 1840*b* is currently combined with the table type receptor 1880*b*, current position information of the X-ray detector 1840*b* corresponds to table position information.

An output unit 1850*b* of the X-ray detector 1840*b* may flicker the assign indicator when the X-ray detector 1840*b* is activated.

The output unit 630 of the workstation 600 may display an X-ray detector icon 1860*b* based on identification information of the X-ray detector 1840*b*, assign indicator thereof, and state information thereof. In detail, the X-ray detector icon 1860*b* may represent that the X-ray detector 1840*b* is a wireless X-ray detector, corresponds to current table position information, displays the assign indicator of a violet color, and has high communication sensitivity and a residual battery capacity of 9% or less. When the X-ray detector 1840*b* is activated, a sub-icon 1870*b* representing the assign indicator may flicker.

Figure 19A:
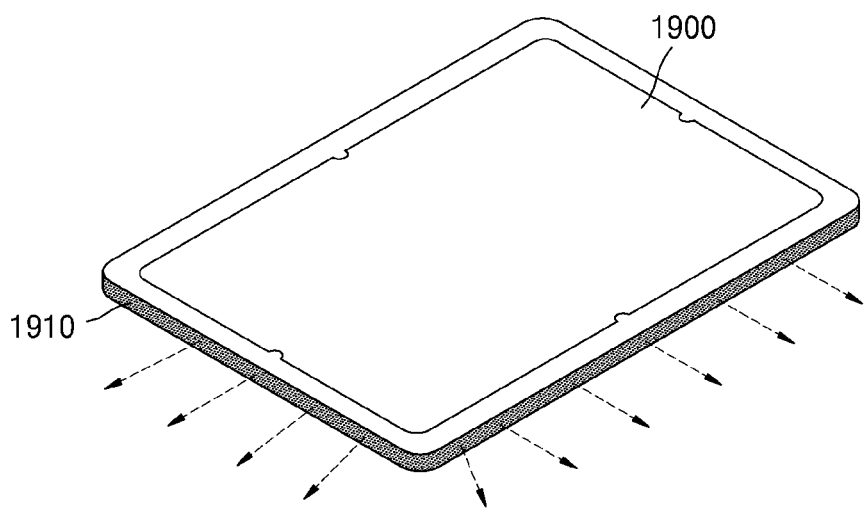
FIGS. 19A-19C illustrate an X-ray detector and an optical waveguide included therein, according to an exemplary embodiment.
Figure 19B:
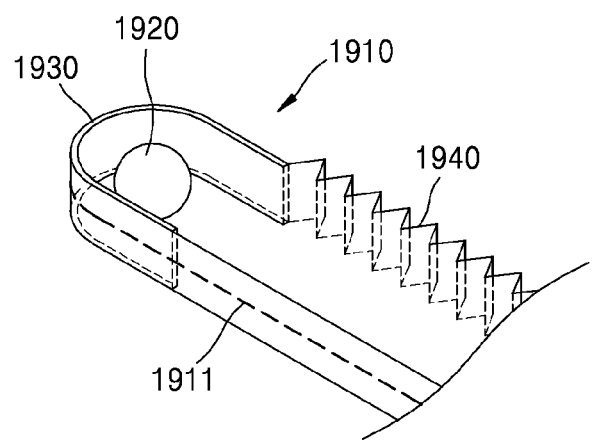
Figure 19C:
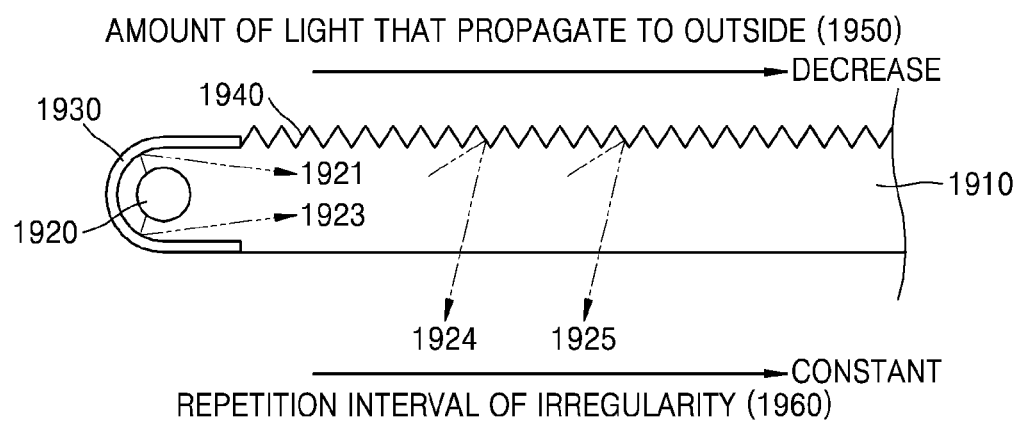

FIGS. 19A-19C illustrate an X-ray detector 1900 and an optical waveguide 1910 included therein, according to an exemplary embodiment.

FIG. 19A illustrates the X-ray detector 1900 capable of displaying an assign indicator by using the optical waveguide 1910 positioned on at least one edge of the X-ray detector 1900.

FIG. 19B is a magnified view of a portion of the optical waveguide 1910, and FIG. 19C illustrates a cross-section cut along a dotted line 1911 of the optical waveguide 1910 of FIG. 19B.

In detail, an output unit of the X-ray detector 1900 may include a light source 1920 generating light of a color indicated by assign indicator information set by a workstation, and the optical waveguide 1910 positioned on at least one edge of the X-ray detector 1900 and guiding the light generated by the light source 1920 to propagate in a certain direction.

The light source 1920 may generate light beams of various colors including the color indicated by the assign indicator information set by the workstation. For example, the light source 1920 may be an LCD or an LED. A controller of the X-ray detector 1900 may control the light source 1920 to generate the color indicated by the assign indicator information set by the workstation.

The optical waveguide 1910 may guide the light generated by the light source 1920 to mostly propagate in a certain direction, by using a total reflection principle.

The optical waveguide 1910 may also include a first reflector 1930 for guiding light to propagate in a certain direction within the optical waveguide 1910. In detail, the first reflector 1930 may set the direction in which light beams generated by the light source 1920 mainly propagate, by reflecting light beams 1921 and 1923 from among the light beams generated by the light source 1920.

In general, in the field of optical communication, an optical waveguide guides light to a destination by minimizing light loss via total reflection which is the main function of the optical waveguide. However, the optical waveguide 1910 included in the output unit of the X-ray detector 1900 needs to propagate some of the light beams generated by the light source 1920 to the outside so that a user may check an assign indicator. Accordingly, the optical waveguide 1910 may include a predetermined structure or reflector for propagating some of the light beams generated by the light source 1920 to the outside. For example, the optical waveguide 1910 may include a transparent body such as a transparent glass or a transparent plastic.

The optical waveguide 1910 may also include an irregularity 1940 on one side thereof, in order to propagate some of the light beams generated by the light source 1920 to the outside. The irregularity 1940 of the optical waveguide 1910 may be repeatedly formed on one side of the optical waveguide 1910.

For example, as illustrated in FIGS. 19B and 19C, when an internal side of the optical waveguide 1910 is formed as the irregularity 1940, light beams 1924 and 1925 reflected by the irregularity 1940 may be incident upon an external side thereof at a reduced angle. Thus, the light beams 1924 and 1925 reflected by the irregularity 1940 may be propagated to the outside, and a user may check the assign indicator via the optical waveguide.

On the other hand, when the external side of the optical waveguide 1910 is formed as an irregularity, the angle at which light is incident upon the irregularity may be reduced. Thus, some light beams incident upon the irregularity may be propagated to the outside, and a user may check the assign indicator via the optical waveguide 1910.

The optical waveguide 1910 may include an elastic body. In detail, the optical waveguide 1910 may include an elastic body capable of performing a buffering function. When the optical waveguide 1910 includes the elastic body, the X-ray detector 1900 may not need a buffer material.

When the output unit of the X-ray detector 1900 displays the assign indicator via the optical waveguide 1910, a user may check the assign indicator of the X-ray detector 1900 at various locations. Thus, the user may more efficiently select an X-ray detector suitable for a photographing environment when the output unit of the X-ray detector 1900 displays the assign indicator by using the optical waveguide 1910 rather than when displaying the assign indicator by simply using an LED or a light-emitting device.

Figure 20A:
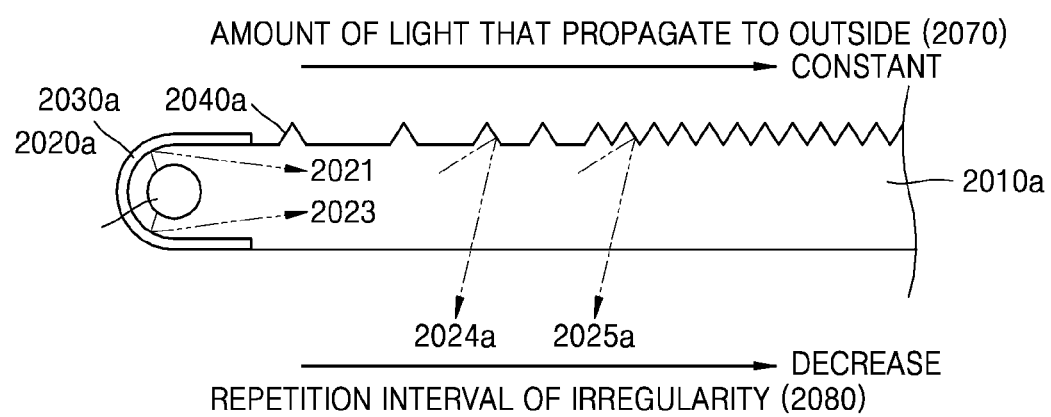
FIGS. 20A and 20B are cross-sectional views of optical waveguides according to another exemplary embodiment.
Figure 20B:
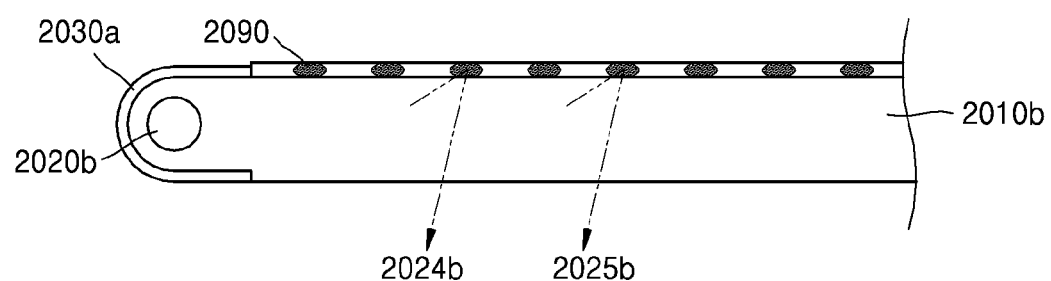

FIGS. 20A and 20B are cross-sectional views of optical waveguides 2010*a* and 2010*b* according to another exemplary embodiment.

The optical waveguides 2010*a* and 2010*b* of FIGS. 20A and 20B may correspond to the optical waveguide 1910 of FIGS. 19A-19C. In detail, a light source 2020*a*, a first reflector 2030*a*, light beams 2021 and 2023 reflected by the first reflector 2030*a*, and light beams 2024*a* and 2025*a* reflected by an irregularity 2040*a* of FIGS. 20A and 20B may correspond to the light source 1920, the first reflector 1930, the light beams 1921 and 1923 reflected by the first reflector 1930, and the light beams 1924 and 1925 reflected by the irregularity 1940 of FIGS. 19A-19C, respectively. Thus, a repeated description thereof will be omitted.

Since light beams generated by the light source 2020*a* propagate to the outside while traveling along the optical waveguide 2010*a*, the amount of light existing within the optical waveguide 2010*a* decreases in a direction away from the light source 2020*a*.

Thus, as illustrated in FIG. 19C, when a repetition interval 1960 of the irregularity 1940 of the optical waveguide 1910 is constant in a direction away from the light source 1920, an amount 1950 of light that propagates to the outside may decrease in the direction away from the light source 1920.

Accordingly, stronger light may propagate in a direction closer to the light source 1920, and weaker light may propagate in a direction away from the light source 1920. However, it is desirable to have a constant amount of light propagates to the outside regardless of distances from the light source 1920.

FIG. 20A illustrates a cross-section of the optical waveguide 2010a including the irregularity 2040a of which a repetition interval 2080 shortens in a direction away from the light source 2020a. In detail, the irregularity 2040a of the optical waveguide 2010a may be formed on one side of the optical waveguide 2010a, and the repetition interval 2080 of the irregularity 2040a of the optical waveguide 2010a may shorten in the direction away from the light source 2020a.

When the repetition interval 2080 of the irregularity 2040a of the optical waveguide 2010a may shorten in the direction away from the light source 2020a, although the amount of light existing within the optical waveguide 2010a decreases, an amount 2070 of light that propagates to the outside may be constant.

In detail, as the repetition interval 2080 of the irregularity 2040a shortens, the probability that the light beams generated by the light source 2020a propagate to the outside of the optical waveguide 2010a increases. In other words, as the repetition interval 2080 of the irregularity 2040a shortens, the probability of total reflection of light decreases. Thus, as the repetition interval 2080 of the irregularity 2040a shortens, although the amount of light existing within the optical waveguide 2010a decreases, the probability that light propagates to the outside of the optical waveguide 2010a increases, and thus the amount 2070 of light that propagates to the outside may be constant regardless of distances from the light source 2020a.

FIG. 20B illustrates a cross-section of the optical waveguide 2010b including a second reflector 2090.

The second reflector 2090 may be positioned at one side of the optical waveguide 2010b and may propagate light generated by a light source 2020b to the outside of the optical waveguide 2010b. In detail, when the second reflector 2090 is positioned on an internal side of the optical waveguide 2010b, light beams 2024b and 2025b reflected by the second reflector 2090 may be incident upon an external side of the optical waveguide 2010b at a decreased angle and thus propagate to the outside of the optical waveguide 2010b.

The second reflector 2090 may be formed of a material having a different refractive index from that of the optical waveguide 2010b. The second reflector may be a mirror, a sticker, paint, or the like.

According to another exemplary embodiment, the optical waveguide 2010b may include the irregularity 2040a on one side thereof and the second reflector 2090 on another side thereof.

Figure 21:
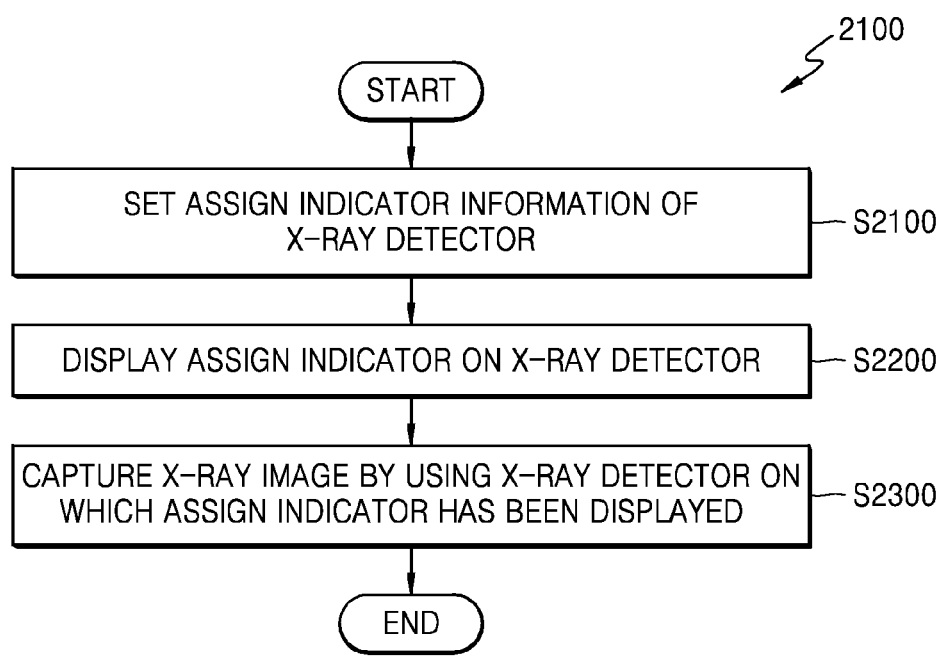
FIG. 21 is a flowchart of a method of capturing an X-ray image, according to an exemplary embodiment.

FIG. 21 is a flowchart of a method 2100 of capturing an X-ray image, according to an exemplary embodiment.

The operations included in the method 2100 are the same as the operations performed in the workstation 600 and the X-ray detector 700 described above with reference to FIGS. 5-20B. Accordingly, descriptions of the method 2100 that are the same as those made with reference to FIGS. 5-20B are not repeated herein.

The method 2100 may include operation S2100 of setting assign indicator information of the X-ray detector 700, based on the identification information of the X-ray detector 700. The operation 2100 may be performed by the workstation 600.

The method 2100 may further include operation S2200 of displaying the assign indicator on the X-ray detector 700 based on the assign indicator information of the X-ray detector 700. The operation S2200 may be performed by the X-ray detector 700.

The method 2100 may further include operation S2300 of capturing the X-ray image by using the X-ray detector 700 on which the assign indicator has been displayed.

As described above, a user may efficiently classify a plurality of X-ray detectors and efficiently select an X-ray detector suitable or an X-ray photographing environment, by using a workstation and an X-ray apparatus according to one or more exemplary embodiments.

The exemplary embodiments can be written as computer programs and can be implemented in general-use digital computers that execute the programs using a computer readable recording medium. For example, it is understood that in exemplary embodiments, one or more units and/or controllers of the above-described apparatuses (e.g., 100, 110) can include circuitry, a processor, a microprocessor, etc., and may execute a computer program stored in a computer-readable medium.

Examples of the computer readable recording medium include magnetic storage media (e.g., ROM, floppy disks, hard disks, etc.), optical recording media (e.g., CD-ROMs, or DVDs), etc.

The exemplary embodiments should be considered in descriptive sense only and not for purposes of limitation. Descriptions of features or aspects within each exemplary embodiment should typically be considered as available for other similar features or aspects in other exemplary embodiments.

While the present invention has been particularly shown and described with reference to exemplary embodiments thereof, it will be understood by those of ordinary skill in the art that various changes in form and details may be made therein without departing from the spirit and scope of the present invention as defined by the appended claims.

What is claimed is:

1. An X-ray system comprising:
   an X-ray detector that is coupleable to, and decoupleable from, a receptor, and including an indicator to output a color that is different than a color output by an indicator of another X-ray detector of the X-ray system to distinguish the X-ray detector from the another X-ray detector; and
   a workstation including a display, and configured to, with the X-ray detector coupled to the receptor, and the indicator of the X-ray detector outputting the color,
      control the display to display an icon with the color output by the indicator of the X-ray detector, and providing position information that, when receptor to which the X-ray detector is coupled is a stand type receptor, indicates that the X-ray detector is in a stand position coupled to a stand type receptor and, when the receptor to which the X-ray detector is coupled is a table type receptor, indicates that the X-ray detector is in a table position coupled to a table type receptor.

2. The X-ray system of claim 1, wherein the workstation is further configured to set the color to be output by the indicator of the X-ray detector.

3. The X-ray system of claim 1, wherein the workstation further comprises:
   an input interface to receive an input for setting the color to be output by the indicator of the X-ray detector; and a controller configured to set the color to be output by the indicator of the X-ray detector in response to the input.

4. The X-ray system of claim 2, wherein the workstation is further configured to transmit information to the X-ray detector to set the color to be output by the indicator of the X-ray detector.

5. The X-ray system of claim 1, wherein the icon includes at least one of a symbol, a character, and an image, that,
when the receptor to which the X-ray detector is coupled is the stand type receptor, indicates that the X-ray detector is in the stand position coupled to the stand type receptor, with the color output by the indicator of the X-ray detector, and,
when the receptor to which the X-ray detector is coupled is the table type receptor, indicates that the X-ray detector is in the table position coupled to the table type receptor, with the color output by the indicator of the X-ray detector.

6. The X-ray system of claim 1, wherein:
when the X-ray detector is in the stand position, the icon incudes a representation of the stand position with the color output by the indicator of the X-ray detector, and
when the X-ray detector is in the table position, the icon includes a representation of the table position with the color output by the indicator of the X-ray detector.

7. The X-ray system of claim 1, wherein the workstation is further configured to control the display to display an icon including at least one of a symbol, a character, and an image, to indicate, prior to the X-ray detector being coupled to the receptor, that the X-ray detector is currently in a position at which the X-ray detector is not coupled to the receptor.

8. The X-ray system of claim 1, wherein the X-ray detector further includes:
a light source to generate light of the color, and
an optical waveguide, positioned on at least one edge of the X-ray detector, through which the light travels to output the light of the color.

9. The X-ray system of claim 1, wherein the X-ray detector further includes an indicator to indicate a connection state of the X-ray detector.

10. The X-ray system of claim 1, wherein the X-ray detector further includes an indicator to indicate at least one of a residual battery capacity of the X-ray detector, a communication sensitivity of the X-ray detector, and an activation state of the X-ray detector.

11. An X-ray system comprising:
an X-ray detector including an indicator to output a color that is different than a color output by an indicator of another X-ray detector of the X-ray system to distinguish the X-ray detector from the another X-ray detector, and the X-ray detector being positionable in a type of position that is at least one of a stand position and a table position to detect an X-ray; and
a workstation including a display, and configured to:
with the indicator of the X-ray detector outputting the color and the X-ray detector being positioned in a type of position to detect an X-ray, control the display to display an icon in the color output by the indicator of the X-ray detector and indicating the type of position in which the X-ray detector is positioned.

12. The X-ray system of claim 11, wherein
when the type of position in which the X-ray detector is positioned is the stand position, the icon includes at least one of a symbol, a character, and an image, to indicate that the X-ray detector is positioned in the stand position, and
when the type of position in which the X-ray detector is positioned is the table position, the icon includes at least one of a symbol, a character, and an image, to indicate that the X-ray detector is positioned in the table position.

13. A workstation of an X-ray system, the workstation being operable with an X-ray detector of the X-ray system, the X-ray detector being coupleable to, and decoupleable from, a receptor, and the X-ray detector including an indicator to output a color that is different than a color output by an indicator of another X-ray detector of the X-ray system to distinguish the X-ray detector from the another X-ray detector, the workstation comprising:
a display; and
a controller configured to, with the X-ray detector coupled to the receptor, and the indicator of the X-ray detector outputting the color,
control the display to display an icon with the color output by the indicator of the X-ray detector, and providing position information that, when the receptor to which the X-ray detector is coupled is a stand type receptor, indicates that the X-ray detector is in a stand position coupled to a stand type receptor and, when the receptor to which the X-ray detector is coupled is a table type receptor, indicates that the X-ray detector is in a table position coupled to a table type receptor.

14. The workstation of claim 13, wherein the controller is further configured to set the color to be output by the indicator of the X-ray detector.

15. The workstation of claim 14, wherein the controller is further configured to transmit information to the X-ray detector to set the color to be output by the indicator of the X-ray detector.

16. A workstation of an X-ray system, the workstation being operable with an X-ray detector of the X-ray system, the X-ray detector being coupleable to, and decoupleable from, a receptor, and the X-ray detector including an indicator to output a color that is different than a color output by an indicator of another X-ray detector of the X-ray system to distinguish the X-ray detector from the another X-ray detector, the workstation comprising:
a display; and
a controller configured to, with the X-ray detector coupled to the receptor, and the indicator of the X-ray detector outputting the color,
control the display to display an icon with the color output by the indicator of the X-ray detector, and indicating a type of the receptor to which the X-ray detector is coupled,
wherein the type of the receptor is a table type or a stand type.

17. The workstation of claim 16, wherein
when the type of the receptor to which the X-ray detector is coupled is the stand type, the icon includes at least one of a symbol, a character, and an image, to indicate that the receptor is the stand type, and
when the type of the receptor to which the X-ray detector is coupled is the table type, the icon includes at least one of a symbol, a character, and an image, to indicate that the receptor is the table type.

18. The workstation of claim 16, wherein the controller is further configured to set the color to be output by the indicator of the X-ray detector.

19. The workstation of claim 18, wherein the controller is further configured to transmit information to the X-ray detector to set the color to be output by the indicator of the X-ray detector.

20. A workstation of an X-ray system, the workstation being operable with an X-ray detector of the X-ray system, the X-ray detector including an indicator to output a color that is different than a color output by an indicator of another X-ray detector of the X-ray system to distinguish the X-ray detector from the another X-ray detector, and the X-ray detector being, positionable in a type of position that is at least one of a stand position and a table position to detect an X-ray, the workstation comprising:

a display; and a controller configured to, with the indicator of the X-ray detector outputting the color and the X-ray detector being positioned in a type of position to detect an X-ray, control the display to display an icon in the color output by the indicator of the X-ray detector and indicating the type of position in which the X-ray detector is positioned.

21. The workstation of claim 20, wherein when the type of position in which the X-ray detector is positioned is the stand position, the icon includes at least one of a symbol, a character, and an image, to indicate that the X-ray detector is positioned in the stand position, and when the type of position in which the X-ray detector is positioned is the table position, the icon includes at least one of a symbol, a character, and an image, to indicate that the X-ray detector is positioned in the table position.

* * * * *

UNITED STATES PATENT AND TRADEMARK OFFICE
CERTIFICATE OF CORRECTION

| | |
|---|---|
| PATENT NO. | : 11,278,251 B2 |
| APPLICATION NO. | : 16/036233 |
| DATED | : March 22, 2022 |
| INVENTOR(S) | : Park et al. |

It is certified that error appears in the above-identified patent and that said Letters Patent is hereby corrected as shown below:

In the Specification

Column 1, Line 9, delete "as now" and insert --as--.

In the Claims

Column 37, Line 11, In Claim 20, delete "being," and insert --being--.

Signed and Sealed this
Tenth Day of May, 2022

Katherine Kelly Vidal
*Director of the United States Patent and Trademark Office*